United States Patent
Setterstrom et al.

(10) Patent No.: US 6,410,056 B1
(45) Date of Patent: *Jun. 25, 2002

(54) CHEMOTHERAPEUTIC TREATMENT OF BACTERIAL INFECTIONS WITH AN ANTIBIOTIC ENCAPSULATED WITHIN A BIODEGRADABLE POLYMERIC MATRIX

(75) Inventors: Jean A. Setterstrom; Elliot Jacob, both of Silver Spring, MD (US); Thomas R. Tice, Birmington, AL (US)

(73) Assignee: The United States of America as represented by the Secretary of the Army, Washington, DC (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/446,148

(22) Filed: May 22, 1995

(Under 37 CFR 1.47)

Related U.S. Application Data

(63) Continuation-in-part of application No. 08/209,350, filed on Jan. 7, 1994, now abandoned, which is a continuation-in-part of application No. 07/493,597, filed on Mar. 15, 1990, now abandoned, which is a continuation-in-part of application No. 06/590,308, filed on Mar. 16, 1984, now abandoned.

(51) Int. Cl.[7] .......................... A61K 9/50; A61K 47/30; B32B 5/16
(52) U.S. Cl. ................. 424/501; 424/502; 428/402.24; 514/772.3
(58) Field of Search ................................ 424/78.1, 457, 424/462, 501, 502; 549/274; 428/402.21; 514/772.3

(56) References Cited

U.S. PATENT DOCUMENTS

| | | | |
|---|---|---|---|
| 3,540,444 A | 11/1970 | Moreland | 128/173 |
| 3,788,315 A | 1/1974 | Laurens | 128/173 H |
| 4,166,800 A | 9/1979 | Fong | 252/316 |
| 4,384,975 A | 5/1983 | Fong | 427/213.36 |
| 4,415,557 A | * 11/1983 | Metzger | 514/274 |
| 4,530,840 A | 7/1985 | Tice et al. | 424/78 |
| 4,542,025 A | 9/1985 | Tice et al. | 424/213.78 |
| 4,585,482 A | 4/1986 | Tice et al. | 106/15.05 |
| 4,622,244 A | 11/1986 | Lapka et al. | 427/213.32 |
| 4,637,905 A | 1/1987 | Gardner | 264/4.3 |

(List continued on next page.)

FOREIGN PATENT DOCUMENTS

EP 0052510 B2 10/1994 ............ A61K/9/50

OTHER PUBLICATIONS

Gilding, Biodegradable polymers for use in surgery–polyglycolic/poly (ac c acid) homo–and copolymers: 1, Polymer, vol. 20, Dec. 1979, pp. 1459–1464.

Biotechnology News, Aug. 22, 1997, vol. 17, No. 20, Topical DNA vaccine elicits immune response.

Hall, et al., Purification and Analysis of Colonization Factor Antigen I, Coli Surface Antigen 1, and Coli Surface ANtigen 3 Fimbriae from Enterotoxigenic Escherichia Coli, Journal of Bacteriology, Nov. 1989, pp. 6372–6374, vol. 171, No. 11.

(List continued on next page.)

Primary Examiner—Thurman K. Page
Assistant Examiner—S. Howard
(74) Attorney, Agent, or Firm—Elizabeth Arwine; Charles H. Harris; John Francis Moran

(57) ABSTRACT

Biodegradable pharmaceutical compositions and method for treating bacterial infections therein.

47 Claims, 6 Drawing Sheets

U.S. PATENT DOCUMENTS

| | | | |
|---|---|---|---|
| 4,675,189 A | 6/1987 | Kent et al. | 424/490 |
| 4,798,786 A | 1/1989 | Tice et al. | 435/177 |
| 4,835,139 A | 5/1989 | Tice et al. | 514/15 |
| 4,863,735 A | 9/1989 | Kohn et al. | 524/422 |
| 4,897,268 A | 1/1990 | Tice et al. | 424/422 |
| 4,938,763 A | 7/1990 | Dunn et al. | 604/891.1 |
| 4,941,880 A | 7/1990 | Burns | 604/143 |
| 5,000,886 A | 3/1991 | Lawter et al. | 264/4.3 |
| 5,019,096 A | 5/1991 | Fox, Jr. et al. | 623/1 |
| 5,059,187 A | 10/1991 | Sperry et al. | 604/290 |
| 5,064,413 A | 11/1991 | McKinnon et al. | 604/70 |
| 5,075,109 A | 12/1991 | Tice et al. | 424/88 |
| 5,102,872 A | 4/1992 | Singh et al. | 514/21 |
| 5,129,825 A | 7/1992 | Discko, Jr. | 433/90 |
| 5,133,701 A | 7/1992 | Han | 604/289 |
| 5,236,355 A | 8/1993 | Brizzolara et al. | 433/80 |
| 5,278,202 A | 1/1994 | Dunn et al. | 523/113 |
| 5,290,494 A | 3/1994 | Coombes et al. | 264/41 |
| 5,360,610 A | 11/1994 | Tice et al. | 424/426 |
| 5,384,133 A | 1/1995 | Boyes et al. | 424/501 |
| 5,407,609 A | 4/1995 | Tice et al. | 264/46 |
| 5,417,986 A | 5/1995 | Reid et al. | 424/499 |
| 5,429,822 A | 7/1995 | Gresser et al. | 424/426 |
| 5,500,228 A | 3/1996 | Lawter et al. | 424/486 |
| 5,538,739 A | 7/1996 | Bodomer et al. | 424/501 |
| 5,639,480 A | 6/1997 | Bodmer et al. | 424/501 |
| 5,643,605 A | 7/1997 | Cleland et al. | 424/489 |
| 5,648,096 A | 7/1997 | Gander et al. | 424/489 |
| 5,650,173 A | 7/1997 | Ramstack et al. | 424/489 |
| 5,688,530 A | 11/1997 | Bodmer et al. | 424/501 |
| 5,693,343 A | 12/1997 | Reid et al. | 424/491 |
| 5,762,965 A | 6/1998 | Burnett et al. | 424/499 |
| 5,811,128 A | 9/1998 | Tice et al. | 424/501 |
| 5,814,344 A | 9/1998 | Tice et al. | 424/501 |
| 5,820,883 A | 10/1998 | Tice et al. | 424/501 |
| 5,853,763 A | 12/1998 | Tice et al. | 424/489 |

OTHER PUBLICATIONS

Evans, et al. Purification and Characterization of the CFR/I Antigen of Enterotoxigenic Escherichia coli, Infection and Immunity, Aug. 1979, pp. 738–748, vol. 25.

Karjalainen, et al., Molecular Cloning and Nucleotide Sequence of the Colonization Factor Antigen I Gene of Escherichia coli, Infection and Immunity, Apr. 1989, pp. 1126–1130, vol. 57.

Jeyanthi, et al., Novel, Burst Free Programmable Biodegradable Microspheres For Controlled Release of Polypeptides, Proceedings Int. Symp. control Release Bioact. Mater. (1996) pp. 351–352/.

Yeh, A novel emulsification–solvent extraction technique for production of protein loaded biodegradable microparticles for vaccine and drug delivery, Journal of Controlled Release, 33 (1005) 437–445.

Yan, Characterization and morphological analysis of protein–loaded poly(lactide–co–glycolide) microparticles prepared by watewr–in–oil–in–water emulsion technique, Journal of Controlled Release, 32 (1994) 231–241.

Wang, et al., Influence of formulation methods on the in vitro controlled release of protein from poly (ester) microspheres Journal of Controlled Release, 17 (1991) 23–32.

Brown, Wonder Drugs' Losing Healing Aura, The Washing Post, Jun. 26, 1995, A section.

Setterstrom, Controlled Release of Antibiotics From biodegradable Microcapsules For Wound infection Control, Chemical Abstracts, 1983, pp. 215–226.

Perez–Casal, et al., Gene Encoding the Major Subunit of CS1 Pili of Human Enterotoxigenic Escherichia Coli, Infection and Immunity, Nov., 1990, pp. 3594–3600, vol. 58, No. 11.

Jordi, et al., Analysis of the first two genes of the CS1 fimbrial operon in human enterotoxigenic Escherichia coli of serotype 0139: H28, FEMS Microbiology Letters 80, (1991) pp. 265–270.

Tan, et al., Mapping the Antigenic Epitopes of Human Dihydrofolate Reductase by Systematic Synthesis of Peptides on solid Supports, The Journal of Biological Chemistry, vol. 265, No. 14, Issue of May 15, pp. 8022–8026 (1990).

McConnel, et al., Antigenic homology within human enterotoxigenic Esherichia coli fimbrial colonization factor antigens: CFA/I, coli–surface–associated antigens (CS)1, CS2, CS4 and CS17, FEMS Microbiology Letters 61 (1989) 105–108.

Van der Zee, Efficient mapping and characterization of a T cell epitope by the simultaneous synthesis of multiple peptides, Eur. J. Immunol. 1989, 19: 43–47.

Cassels, et al., Analysis of Escherichia coli Colonization Factor Antigen I Linear B–Cell Epitopes, as Determined by Primate Responses, following Protein Sequence Verification, Infection and Immunity, Jun. 1992, pp. 2174–2181, vol. 60, No. 6.

Romagnoli, et al. Peptide–MHC Interaction: A Rational Approach to Vaccine Design, Inter, RE. Immunol. 6, 1990, 00 61–73.

Maister, First Oral AIDS Vaccine Trials Near, BioWorld Today, Tuesday, Apr. 19, 1994, p. 4.

Rognan, et al., Molecular Modeling of an Antigenic Complex Between a Viral Peptide and a Class I Major Histocompatibility Glycoprotein, Proteins Structure, Function and Genetics 13 70–85 (1992).

Brown, A hypothetical model of the foreign antigen biinding site of Class II histocompatibility molecules, Nature, vol. 332, Apr. 28 1988, pp. 845–850.

* cited by examiner

CHEMOTHERAPEUTIC TREATMENT OF BACTERIAL INFECTIONS WITH AN ANTIBIOTIC ENCAPSULATED WITHIN A BIODEGRADABLE POLYMERIC MATRIX

I. GOVERNMENT INTEREST

The invention described herein may be manufactured, used and licensed by or for the Government for Governmental purposes without the payment to us of any royalties thereon.

II. CROSS REFERENCE

This Application is a continuation in part of U.S. patent applications Ser. No. 08/209,350, filed Jan. 7, 1994, now abandoned which in turn is a continuation-in-part of U.S. patent application Ser. No. 07/493,597, filed Mar, 15, 1990, now abandoned, which in turn is continuation-in-part of U.S. patent application Ser. No. 06/590,308, filed Mar. 16, 1984, now abandoned.

III. FIELD OF THE INVENTION

This invention relates to antibacterial antibiotics encapsulated within a biodegradable polymeric matrix.

IV. BACKGROUND OF THE INVENTION

One of the most difficult types of wounds to treat is characterized by the presence of infection, devitalized tissue, and foreign-body contaminants. Local application of encapsulated antibiotics to an area infected with bacteria provides immediate, direct, and sustained dosing which targets the antibiotic to the wound site (soft or hard tissue), and minimizes problems inherent in systemic drug administration. Additionally, by encapsulating antibiotics and applying them directly to the wound site one sees a significant reduction of nonspecific binding of drug to body proteins a phenomena that is commonly observed following the systemic administration of free drugs that are in route to infected site.

To prevent infection, in bone and soft tissue systemic antibiotics must be administered within 4 hours after wounding when circulation is optimal. This has been discussed by J. F. Burke in the article entitled "The Effective Period of Preventive Antibiotic Action in Experimental Incisions and Dermal Lesions", *Surgery*, Vol. 50, Page 161 (1961). If treatment of bacterial infections is delayed, a milieu for bacterial growth develops which results in complications associated with established infections. (G. Rodeheaver et al., "Proteolytic Enzymes as Adjuncts to Antibiotic Prophylaxis of Surgical Wounds", *American Journal of Surgery*, Vol. 127, Page 564 (1974)). Once infections are established it becomes difficult to systemically administer certain antibiotics for extended periods at levels that are safe and effective at the wound site. Unless administered locally, drugs are distributed throughout the body, and the amount of drug hitting its target is only a small part of the total dose. This ineffective use of the drug is compounded in the trauma patient by hypoyolemic shock, which results in a decreased vascular flow to tissues. (L. E. Gelin et al., "Trauma Workshop Report:Schockrheology and Oxygen Transport", *Journal Trauma*, Vol. 10, Page 1078 (1970)).

Additionally, infections caused by multiple-antibiotic resistant bacteria are on the up-swing and we are on the verge of a potential world-wide medical disaster. According to the Centers for Disease Control, 13,300 patients died in U.S. hospitals in 1992 from infections caused by antibiotic-resistant bacteria. Methicillin-resistant *S. aureus* (MRSA) is rapidly emerging as the "pathogen of the 90's":

a. Some major teaching hospitals in U.S. report that up to 40$ of strains of *S. aureus* isolated from patients are resistant to methicillin. Many of these MRSA strains are susceptible only to a single antibiotic (vancomycin).

b. Should MRSA also develop resistance to vancomycin, the mortality rate among patients who develop MRSA infections could approach 80%.

Moreover, Vancomycin resistance is on the up-swing:

a. 20% of Enterococci are now resistant to vancomycin b. In 1989, only one hospital in New York city reported vancomycin-resistant Enterococci. By 1991, the number of hospitals reporting vancomycin resistance rose to 38.

c. transfer of vancomycin-resistant gene (via plasmid) has been shown experimentally between Enterococcus and *S. aureus*. Many major pharmaceutical companies around the world have either completely eliminated or significantly reduced their r & d programs in the area of antibiotic research. According to a 1994 report by the Rockefeller University Workshop in Multiple Antibiotic Resistant Bacteria, we are on the verge of a "medical disaster that would return physicians back to the pre-penicillin days when even small infections could turn lethal due to the lack of effective drugs."

Despite recent advances in antimicrobial therapy and improved surgical techniques, osteomyelitis (hard tissue or bone infection) is still a source of morbidity often necessitating lengthy hospitalization. The failure of patients with chronic osteomyelitis to respond uniformly to conventional treatment has prompted the search for more effective treatmnent modalities. Local antibiotic therapy with gentamicin-impregnated poly(methylmethacrylate) (PMMA) bead chains (SEPTOPAL™, E. Merck, West Germany) has been utilized in Germany for the treatment of osteomyelitis for the past decade and has been reported to be efficacious in several clinical studies. The beads are implanted into the bone at the time of surgical intervention where they provide significantly higher concentrations of gentamicin than could otherwise be achieved via systemic administration. Serum gentamicin levels, on the other hand, remain extremely low thereby significantly reducing the potential for nephro- and ototoxicity that occurs in some patients receiving gentamicin systemically. Since SEPTOPAL™ is not currently approved by the Food and Drug Administration for use in the United States, some orthopedic surgeons in this country are fabricating their own "physician-made beads" for the treatment of chronic osteomyelitis. A major disadvantage of the beads, however, is that because the PMMA is not biodegradable it represents a foreign body and should be removed at about 2-weeks postimplantation thereby necessitating in some cases an additional surgical procedure. A biodegradable antibiotic carrier, on the other hand, would eliminate the need for this additional surgical procedure and may potentially reduce both the duration as well as the cost of hospitalization.

The concept of local, sustained release of antibiotics into infected bone is described in recent literature wherein antibiotic-impregnated PMMA macrobeads are used to treat chronic osteomyelitis. The technique as currently used involves mixing gentamicin with methylmethacrylate bone cement and molding the mixture into beads that are 7 mm in diameter. These beads are then locally implanted in the infected site at the time of surgical debridement to serve as treatment. There are, however, significant problems with this method. These include: 1) initially, large amounts of antibiotics diffuse from the cement but with time the amount of antibiotic leaving the cement gradually decreases to sub-therapeutic levels; 2) the bioactivity of the antibiotic gradually decreases; 3) methylmethacrylate has been shown to decrease the ability of polymorphonuclear leukocytes to phagocytize and kill bacteria; 4) the beads do not biodegrade and usually must be surgically removed; and 5) the exothermic reaction that occurs during curing of methymethacrylate limits the method to the incorporation of only thermostable antibiotics (primarily aminoglycosides). Nevertheless, preliminary clinical trials using these beads indicate that they are equivalent in efficacy to long term (4–6 weeks) administration of systemic antibiotics.

V. SUMMARY OF THE INVENTION

This invention relates to a novel pharmaceutical composition, a micro- or macrocapsule/sphere formulation, which comprises an antibiotic encapsulated within a biodegradable polymeric matrix such as poly (DL-lactide-co-glycolide) (DL-PLG) and its use in the effective pretreatment of animals to prevent bacterial infections and the posttreatment of animals (including humans) with bacterial infections. Microcapsules and microspheres are usually powders consisting of spherical particles of 2 millimeter or less in diameter, usually 500 micrometer or less in diameter. If the particles are less than 1 micron, they are often referred to as nanocapsules or nanospheres. For the most part, the difference between microcapsules and nanocapsules is their size; their internal structure is about the same. Similarly, the difference between microspheres and nanospheres is their size; their internal structure is about the same.

A microcapsule (or nanocapsule) has its encapsulated material, herein after referred to as agent, centrally located within a unique membrane, usually a polymeric membrane. This membrane may be termed a wall-forming material, and is usually a polymeric material. Because of their internal structure, permeable microcapsules designed for controlled-release applications release their agent at a constant rate (zero-order rate of release). Also, impermeable microcapsules can be used for rupture-release application. Hereinafter, the term microcapsule will include nanocapsules, and particles in general that comprise a central core surrounded by a unique outer membrane.

A microsphere has its agent dispersed throughout the particle; that is, the internal structure is a matrix of the agent and excipient, usually a polymer excipient. Usually controlled-release microspheres release their agent at a declining rate (first-order). But microspheres can be designed to release agents at a near zero-order rate. Microspheres tend to be more difficult to rupture as compared to microcapsules because their internal structure is stronger. Hereinafter, the term microspheres will include nanospheres, microparticles, nanoparticles, microsponges (porous microspheres) and particles in general, with an internal structure comprising a matrix of agent and excipient.

One can use other terms to describe larger microcapsules or microspheres, that is, particles greater than 500 micrometer to 7 millimeter or larger. These terms are macrocapsules, macrospheres, macrobeads and beads. Macrocapsules, macrospheres, macrobeads and beads will be used interchangably herein.

VI. DETAILED DESCRIPTION OF THE INVENTION

More particularly, the applicants have discovered efficacious pharmaceutical compositions wherein the relative amounts of antibiotic to the polymer matrix are within the ranges of 5 to 60 preferred that relative ratio between the lactide and glycolide component of the poly(DL-lactide-co-glycolide) is within the range of 40:60 to 100:0, most preferably. Applicants' most preferred composition consists essentially of 30 to 40(core loading) and 60 to 70 poly(DL-lactide-co-glycolide) (DL-PLG). However, it is understood that effective core loads for other antibiotics will be influenced by the nature of the drug, the microbialetiology and type of infection being prevented and/or treated. From a biological perspective, the DL-PLG excipient is well suited for in vivo drug release because it elicits a minimal inflammatory response, is biologically compatible, and degrades under physiologic conditions to products that are nontoxic and readily metabolized. Similar polymeric compositions which afford in vitro release kinetics, as discussed below for DL-PLG, are considered by applicants to be within the scope of this invention. Applicants have discovered that antibiotic encapsulated microcapsules/spheres or macrocapsules/spheres (beads) having a diameter within the range of about 40 microns to about 7 millimeters to be especially useful in the practice of this invention.

Surprisingly, applicants have discovered an extremely effective method of treating bacterial infections of soft-tissue or (bone osteomyelitis) and preventing these type infections with antibiotics such as beta-lactams, aminoglycosides, polymyxin-B, amphotericin B, aztreonam, cephalosporins, chloramphenicol, fusidans, lincosamides, macrolides, metronidazole, nitro-furantion, Imipenem/ cilastin, quinolones, rifampin, polyenes, tetracycline, sulfonamides, trimethoprim, vancomycin, teicoplanin, imidazoles, and erythromycin 1) micro- and macroencapsulated or 2) micro- and macrospheres formulated within a polymeric matrix such as a poly(DL-lactide-co-glycolide), which has been formulated to release the antibiotic at a controlled, programmed rate over a desirable extended period of time. The microcapsules/spheres have been found to be effective when applied locally, including topically, to open contaminated wounds thereby facilitating the release of the antibiotic from multiple sites within the tissue in a manner which concentrates the antibiotic in the area of need. Similarly, the encapsulated antibiotics of this invention both in the microcapsule/sphere and macrocapsule/sphere (bead) form are effective for the prevention and treatment of orthopedic infections that include osteomyelitis, contaminated open fractures, and exchange revision arthroplasty. The macrocapsules/sphere form offers the same advantages as the microcapsule/sphere, but offers in addition the option to the surgeon of using the subject invention as a packing material for dead space. The subject invention offers an optimal treatment for orthopaedic infections because release of the antibiotic from the micro- or macrocapsule/sphere is completely controllable over time; antibiotic can be encapsulated into the sphere; the sphere can be made of any size; and unlike the methylmethracrylate beads, the subject invention biodegrades over time to nontoxic products and does not have to be surgically removed from the treated site. Since virtually any antibiotic can be encapsulated into the polymer the instant invention can be used to sustain release all known antibiotics.

Applicants have discovered and/or contemplate that local application of microencapsulated or macroencapsulated antibiotic provides immediate, direct, and sustained dosing which targets the antibiotic to the pre- or post infected soft-tissue or bone site, and minimizes problems inherent in systemic drug administration. It appears to applicants that there is a significant reduction of nonspecific binding of antibiotic to body proteins, as compared to systemic administered antibiotics, while in route to targeted sites. Additionally, antibiotics with short half-lives can be used more efficiently, undesirable side-effects can be minimized, and multiple dosing can be eliminated.

The ability to concentrate the antibiotic within the wound site ensures an extended period of direct contact between an effective antibiotic level and the infecting microorganisms. Many drugs have a therapeutic range below which they are ineffective and above which they are toxic. Oscillating drug levels, commonly observed following systemic administration, may cause alternating periods of ineffectiveness and toxicity. A single dose of applicants' controlled-release preparation can maintain the antibiotic in the desired therapeutic range. Applicants have discovered that microencapsulated or macroencapsulated heavy concentrated doses of antibiotics are effective for the treatment and prevention of infections caused by antibiotic-resistant bacteria.

Topical application of the antibiotic microcapsule/sphere formulation to infected wounds allows local application of the antibiotic in a single dose, whereby an initial burst of antibiotic for immediate soft- or hard-tissue perfusion, followed by a prolonged, effective level of antibiotic is achieved in the tissue at the wound site. Applicants contemplate herein antibiotic microcapsules/spheres and macrocapsules/spheres consisting of an antibiotic and DL-PLG and the summarized results of illustrative experiments that evaluated the prototype microcapsules in vitro and in vivo.

The subject invention is successful in preventing and treating (1) soft-tissue infections, (2) osteomyelitis, and (3) infections surrounding internally fixed fractures. These results were confirmed using the microcapsule/sphere form of the encapsulated antibiotics. The microcapsule/sphere and macrocapsule/sphere are also of value in numerous other applications including soft-tissue infections that involve, but are not limited to the prevention and treatment of (1) subcutaneous infections secondary to contaminated abdominal surgery, (2) infections surrounding prosthetic devices and vascular grafts, (3) ocular infections, (4) topical skin infections, and (5) in oral infections such as pericoronitis and periodontal disease.

The biodegradation rate of the excipient is controllable because it is related to the mole ratio of the constituent monomers, the excipient molecular weight and the surface area of the microcapsules produced. Microcapsules/spheres with diameters of 250 micrometers or less are amendable to direct administration to a wound by a shaker-type dispenser or aerosol spray. The macrocapsules/spheres are manually placed in the tissue on bone by the surgeon at the time of surgical debridement. Due to the unique pharmacokinetic advantages realized with the continuous delivery of antibiotic into tissue from a controlled-release vehicle, applicants have found that a small total dose is required to obtain an optimal therapeutic effect.

VII. BRIEF DESCRIPTION OF THE DRAWINGS

FIG. 1 shows the in vitro release of [$^{14}$C]-ampicillin anhydrate from sterilized microcapsules/spheres (45 to 106 micrometers in diameter) into 0.1 molar potassium phosphate receiving fluid (pH 7.4) maintained at 37° C. The microcapsules consisted of about 10 weight percent ampicillin anhydrate and about 65 weight percent 53:47 DL-PLG polymer.

Serum Cefazolin Levels.

Figure 6:
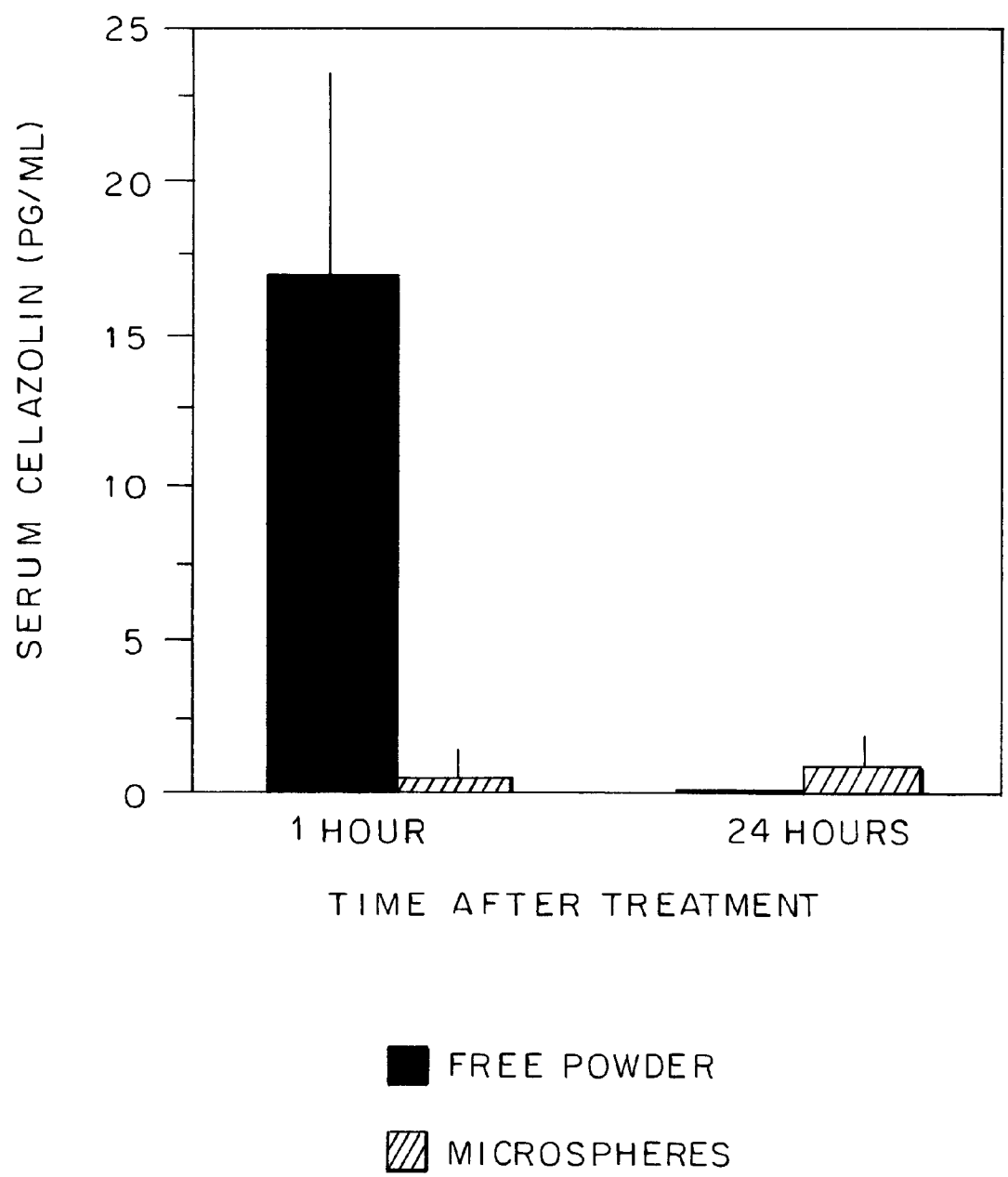

FIG. 6 shows the mean serum concentrations of cefazolin that were measured at 1 hour and 24 hours following local antibiotic therapy with either CZ microspheres (Group A) or free CZ powder (Group B) in the rabbit fracture-fixation model. At 1 hour, the mean serum cefazolin levels were approximately 32 times higher for the Group B animals who had received local antibiotic therapy with free CZ powder (18.7±6.1 ug/ml) as compared to the Group A animals who were treated with CZ microspheres) 0.57±0.27 ug/ml). This difference in the mean serum cefazolin levels between the two groups was statistically significant (p=0.0023) by Student's t test. At 24 hours following local treatment, no cefazolin was detected in the sera of the rabbits who had received free CZ powder (Group B), however, low cefazolin concentrations were detected in the sera of Group A animals who were treated with the CZ microspheres. It is evident. from the data that the free antibiotic diffuses rapidly from the wound and is absorbed into the systemic circulation, whereas, the microspheres remain localized and continue to release low but measurable levels of antibiotic for an extended time interval.

VII. DETAILED DESCRIPTION OF EXAMPLES

The herein offered examples provide methods for illustrating, without any implied limitation, the practice of this invention in the treatment of bacterial wound infections.

The profile of the representative experiments have been chosen to illustrate the antibacterial activity of antibiotic-polymeric matrix composites.

All temperatures not otherwise indicated are in degrees Celcius (° C.) and parts or percentages are given by weight.

MATERIALS AND METHODS

A. Microcapsules/spheres. The ampicillin anhydrate microspheres used in these studies (Composite Batch D 856-038-1) consisted of 30.7 wt in a copolymer of 52:48 poly (DL-lactideco-glycolide). The size of the microspheres ranged from 45 to 150 microns and they were sterilized with 2.0 Mrad of gamma irradiation.

Animals. New Zealand white rabbits (Dutchland Laboratories, Denver, Pa.), weighing 2.0 to 2.5 kg each, were used. The animals were housed in individual cages and were fed a standard laboratory diet. The experiments described herein were conducted in accordance with the principles set forth in the Guide for the Care and Use of Laboratory Animals.

EXAMPLE 1

Osteomyelitis Model. The technique used to produce osteomyelitis was a modification of the procedure described previously by Norden. Briefly, New Zealand white rabbits (2.0–2.5 kg, each) were anesthetized with ketamine hydrochloride and xylazine and access to the medullary canal was gained by inserting an 18-guage Osgood needle (Becton Dickinson Corp., Rutherford, N.J.) into the right proximal tibial metaphysis. Through this needle was injected 0.1 ml of 5 Pharmaceuticals, Tenaf ly, N.J.) followed by injection of approximately $5 \times 10^6$ CFU of S. aureus ATCC 6538P. The hole in the bone was sealed with bone wax and each animal received a single subcutaneous injection of 3-ml TORBUTROL™ (A. J. Buck, Hunt Valley, Md.) for postoperative pain control. Antibiotic therapy was then initiated either immediately or was delayed for 7-days as described in detail below.

EXAMPLE 2

Immediate Antibiotic Therapy. The initial experiment was designed to evaluate the efficacy of local therapy with microencapsulated ampicillin for the prevention of experimental osteomyelitis. A total of 31 rabbits were infected in the right proximal tibia with sodium morrhuate and S. aureus and treatment was initiated immediately as follows:

Group A (n=6) received three daily subcutaneous injections (75 mg/kg/day) of aqueous sodium ampicillin (Polycillin-N™, Bristol Laboratories, Syracuse, N.Y.) at 8-hour intervals for 14 consecutive days;]

Group B (n=7) received a single intramedullary injection of 100 mg of microencapsulated ampicillin containing an equivalent of 30.7 mg of ampicillin anhydrate. The microcapsules/ spheres were suspended in 0.2-ml of 2injection vehicle) and were then injected into the medullary canal through the same needle that was used to inject the sclerosing agent and bacteria;

Group C (n=4) received a single intramedullary injection of 0.12 ml (30.7 mg) of aqueous sodium ampicillin (representing the unencapsulated free drug); and Groups D, X, and F (n=14) served as controls and received either an intramedullary injection of placebo microcapsules (100 mg) without antibiotic; injection vehicle (0.2 ml) without antibiotic; or no treatment.

The animals were observed for a total of 8-weeks during which time roentgenograms were obtained to evaluate the progression of the disease. All surviving animals were euthanized intravenously at two months postinfection with T-61 euthanasia solution (1 mg/kg/iv) and the tibiae were harvested for bacteriological analysis as described below.

EXAMPLE 3

Delayed Antibiotic Therapy Without Debridement. In the second experiment, a total of 30 rabbits were injected in the right proximal tibia with sodium morrhuate and S. aureus and the infection was allowed to become established for 7-days. On Day 7, the animals were reanesthetized and an incision was made over the patellar tendon to expose the tibial tuberosity. A 5-mm drill hole was made in the tibial tuberosity and a trocar, measuring approximately 15 centimeters in length, was inserted into the medullary canal to obtain a marrow specimen for culture. The animals were then randomly assigned to the following treatment groups:

Group A (n=8) received three daily subcutaneous injections of aqueous sodium ampicillin (75 mg/kg/day) at 8-hour intervals for 14-days;

Group B (n=8) received an intramedullary application of 150 mg of microencapsulated ampicillin containing an equivalent of 45 mg of ampicillin anhydrate. The microcapsules were initially suspended in 0.2 ml of the injection vehicle and then aspirated into a sterile trocar. The trocar was then inserted into the medullary canal through the drill hole in the tibial tuberosity;

Group C (n=8) received an intramedullary application of 0.18 ml (45 mg) of aqueous sodium ampicillin which was also delivered into the canal with a trocar; and Group D (n=6) served as controls and received no treatment.

Following the implantation of the antibiotics into the medullary canal, the hole in the tibial tuberosity was sealed with bone wax and the incision site was closed with 3-0 Dexon sutures. All of the surviving animals were euthanized 8 weeks following the initiation of treatment and the tibiae were harvested for bacteriological analysis.

EXAMPLE 4

Delayed Antibiotic Therapy With Debridement. Because standard treatment of chronic osteomyelitis requires the surgical removal of devitalized osseous tissue, the objective of this experiment was to evaluate the efficacy of local antibiotic therapy with microencapsulated ampicillin anhydrate when used in conjunction with debridement. A total of 30 rabbits were injected in the right proximal tibia with sodium morrhuate and S. aureus and the infection was allowed to establish for 7 days. On Day 7 each animal underwent a standardized surgical debridement of the infected tibia. The animals were anesthetized and an incision was made to expose the medial aspect of the tibia. A Hall drill was used to decorticate approximately one-third of the bone thereby creating a channel that extended the length of the bone. The canal was thoroughly debrided with a curette and then irrigated with 20 ml of sterile saline. Cultures of the marrow were obtained at this time for bacteriological analysis. Immediately following completion of the debridement procedure, the animals were randomly assigned to the following treatment groups:

Group A (n=10) received 150 mg of microencapsulated ampicillin containing an equivalent of 45 mg of ampicillin anhydrate. The microcapsules were suspended in 0.2-ml of injection vehicle and were then implanted into the debrided canal with a sterile trocar;

Group B (n=10) received 45 mg of unencapsulated sodium ampicillin in powder form which was applied uniformly into the debrided canal; and Group C (n=5) and Group D (n=5) served as controls and received either an intramedullary application of placebo microcapsules (150 mg) without antibiotic or (2) an injection vehicle (0.2 ml) without antibiotic, respectively.

Immediately following the implantation of the materials into the medullary canal, the incision site was closed with 3-0 Dexon sutures and each animal received 3-ml of Torbutrol™ for 3 consecutive days for postoperative pain. The animals were euthanized at 8 weeks following the initiation of treatment and the tibiae were harvested for bacteriological evaluation.

EXAMPLE 5

Roentaenographic Evaluation. Radiographs of the infected tibiae were obtained at various time intervals and were evaluated by a board certified skeletal radiologist (LMM) using a grading system that was originally developed by Norden et al. Four radiographic parameters (sequestrum formation, periosteal reaction, bone destruction, and extent of disease) were evaluated for each animal and a numerical value was assigned for each variable. The scores were then totaled to arrive at an overall radiographic severity score. The highest total score possible with this grading scheme was +7 and reflected the maximum degree of radiographic severity.

EXAMPLE 6

Cultures of Bone. For bacteriological evaluation, the tibiae were dissected free of adherent soft-tissue and the surface of the bone was cleaned with alcohol pads. The bone was then weighed and crushed to small pieces with a sterile mortar and pestle. The crushed bone was suspended in 5 ml of sterile saline and serial 10-fold dilutions were prepared in 0.1 Each dilution (0.1 ml) was then streaked onto both sheep blood agar and mannitol salt agar plates which were incubated aerobically at 37° C. for 24 hours. The recovery of any *S. aureus* colonies from the bones was evidence of a persistent osseous infection and was considered as a treatment failure.

EXAMPLE 7

Measurement of Serum Ampicillin Levels. In the experiment where local antibiotic therapy was used in conjunction with debridement, serum levels of ampicillin were measured for all of the animals treated with either an intramedullary application of microencapsulated ampicillin anhydrate (Group A) or unencapsulated free drug (Group B). Serum was obtained from all animals at 1 hour, 1 day, and 7 days following the implantation of the antibiotics into the tibiae and serum ampicillin levels were measured using the agar-well diffusion assay described previously in detail by Bennett et al. A standard curve was constructed relating the size of the zones of inhibition obtained with a series of ampicillin standards tested against *Sarcina lutea* ATCC 9341 as the reference organism. Ampicillin concentrations in the test sera were then calculated from this standard curve.

RESULTS OF EXAMPLES 1 THROUGH 7

Immediate Antibiotic Therapy. The results of the initial experiment showing the effect of immediate parenteral versus local ampicillin therapy for the prevention of experimental osteomyelitis are presented in Table 2. Radiographic changes were initially detected in the control animals (Groups D, E, and F) at 2 weeks postinfection and consisted predominantly of periosteal reaction. By 7 weeks, however, the majority of the control animals (75 scores ranging from +5.25 to +7.00 indicating extensive osseous involvement. Radiographic evidence of osteomyelitis was absent in animals that received either a 14 day course of parenteral ampicillin therapy (Group A) or those that received an intramedullary injection of unencapsulated ampicillin (Group C). Only a minimal periosteal reaction was noted at day 42 for Group B animals that received an intramedullary injection of microencapsulated ampicillin, however, all other radiographic parameters were found to be within normal limits. Cultures of the tibiae at 8 weeks following the initiation of treatment showed that all of the animals treated with either a 14 day course of parenteral ampicillin therapy or a single intramedullary injection of microencapsulated ampicillin had sterile bone cultures. Free unencapsulated ampicillin, injected locally into the bone, was also effective and sterilized the tibiae of 3 of 4 (75 In contract, all 13 surviving control animals in Groups D, E, and F developed culture-positive osteomyelitis with *S. aureus* counts ranging from $1.3\times10^6$ to $2.0\times10^7$ CFU recovered per gram of bone.

Delayed Antibiotic Therapy Without Debridement. Table 3 shows the results of the experiment when antibiotic therapy was delayed for 7 days postinfection and was then initiated without debridement. Of the 8 animals in Group A that received a 14 day course of parenteral ampicillin therapy, 6 (75 *aureus* bone cultures. Only 2 of these animals survived the entire length of the experimental protocol; six animals died within 1–2 weeks of completing their antibiotic therapy after developing profuse diarrhea. Of the 7 surviving rabbits in Group C that received an intramedullary application of 45 mg of unencapsulated ampicillin, 5 (71 with a single intramedullary application of microencapsulated ampicillin anhydrate (Group B) sterilized the tibiae of 4 of 8 (50 of *S. aureus* recovered from the tibiae of the other animals in this group as compared with the controls (Group D). All of the control animals developed osteomyelitis with an average of $2.8\times10^5$ CFU of *S. aureus* recovered per gram of bone. A Chi square analysis of the proportion of animals in each treatment group with positive bone cultures showed no statistically significant differences among the groups (p=0.23).

Delayed Antibiotic Therapy With Debridement. In this experiment we evaluated the effect of local antibiotic therapy when used in conjunction with debridement for the treatment of a 7-day established osseous infection. Bacteriological cultures of the tibiae at the time of debridement (before antibiotic therapy was initiated) yielded *S. aureus* in 29 of 30 (97 shown in Table 4, all 10 of the animals in Group A that were treated with debridement plus microencapsulated ampicillin anhydrate had sterile bone cultures. In contrast, of the 10 animals in Group B that were treated with debridement plus unencapsulated ampicillin only 3 had sterile bone cultures whereas 7 developed culture-positive osteomyelitis. A Chin square analysis showed a statistically significant difference (p<0.01) in the proportion of animals with sterile bone cultures in the microencapsulated ampicillin treated group as compared with the group that was treated with the unencapsulated form of the antibiotic. Debridement alone, without local antibiotic therapy, was not effective for the treatment of this established osseous infection with all 10 control animals (Groups C and D) developing cultureposi- tive osteomyelitis.

Serum Ampicillin Levels. In the experiment where local antibiotic therapy was initiated in conjunction with debridement, serum concentrations of ampicillin were measured for all animals that received either an intramedullary application of microencapsulated ampicillin anhydrate or an equivalent dose of unencapsulated free ampicillin. The data is presented in FIG. 1. Serum levels of ampicillin were only detected at 1-hour after the implantation of the antibiotics into the tibiae. At this time interval, the mean serum concentration of ampicillin in the Group B animals that received 45 mg of unencapsulated ampicillin (.79+0.24 micrograms/ml) was approximately 7-fold higher than the mean serum ampicillin concentration of the Group A animals that received an equivalent dose of the microencapsulated form of the antibiotic (0.11+0.08 micrograms/ml).

DISCUSSION RELATED TO EXAMPLES 1 THROUGH 7

Previous attempts to develop a biodegradable antibiotic delivery system for the local treatment of bone infections have met with only limited success. Zilch and Lambiris reported on the treatment of 46 patients with chronic osteomyelitis using a biodegradable fibrin-cefotaxim compound that was implanted into the bone at the time of surgical intervention and reported healing in only 67 limitation of this system was the rapid diffusion of the antibiotic from the fibrin carrier. High concentrations of cefotaxim could only be maintained locally in the would exudate for up to 72 hours. In a separate study, Dahners and Funderburk implanted gentamicin-loaded plaster of paris into the tibiae of rabbits with established staphylococcal osteomyelitis. Although they observed clinical and roentgenographic improvements as compared with nontreated controls, nevertheless, 80 animals treated with the gentamicin-loaded plaster of paris developed culture-positive osteomyelitis. Recently Gerhart et al. evaluated poly(propylenefumarate-co-methylmethacrylate) (PPF-MMA), as a potential biodegradable carrier for antibiotics. Following the subcutaneous implantation of gentamicin- or vancomycin-loaded cylinders of PPF-MMA in rats, high concentrations of each antibiotic were detected locally in the wound exudate while serum antibiotic levels remained low. Although the PPF-MMA appears promising as a potential biodegradable antibiotic carrier, the efficacy of this system remains to be demonstrated in an experimental animal model of osteomyelitis.

In the present application we evaluated biodegradable microspheres of poly(DL-lactide-co-glycolide), containing 30.7 weight percent ampicillin anhydrate, in an experimental osteomyelitis model of the rabbit tibia. In the initial experiment where treatment was initiated immediately following the injection of S. aureus into the medullary canal, a single intramedullary injection of 100 mg of microencapsulated ampicillin effectively prevented the establishment of osteomyelitis in 100 of the animals tested (Table 2). Although a 14 day course of parenteral ampicillin therapy also prevented osteomyelitis in all animals, the total dose of antibiotic administered to these animals (1,050 mg) was 34 times higher than the dose administered to the animals treated locally with the ampicillin-loaded microcapsules (30.7 mg).

In the second experiment, where antibiotic therapy was delayed for 7 days and was instituted without debridement, a 14 day course of parenteral ampicillin therapy resulted in a 75 treatment failure rate (Table 3). Free unencapsulated ampicillin, implanted locally into the bone, was also ineffective with 71 these animals developing culture-proven osteomyelitis. A single intramedullary application of microencapsulated ampicillin, on the other hand, sterilized the tibiae of 50 significantly reduced the mean number of S. aureus colonies recovered from the tibiae of the other animals in this group. It is noteworthy that all animals treated locally with microencapsulated ampicillin anhydrate survived the duration of the experimental protocol without developing adverse side-effects. In contrast, 6 of 8 (75 parenteral ampicillin died within 1 to 2 weeks of completing their antibiotic therapy. The cause of death in these animals was most likely antibiotic-induced diarrhea resulting from colonization of the normal intestinal flora by *Clostridium difficilc*, a phenomenon that has been previously noted with rabbits receiving parenteral ampicillin therapy.

Figure 5:
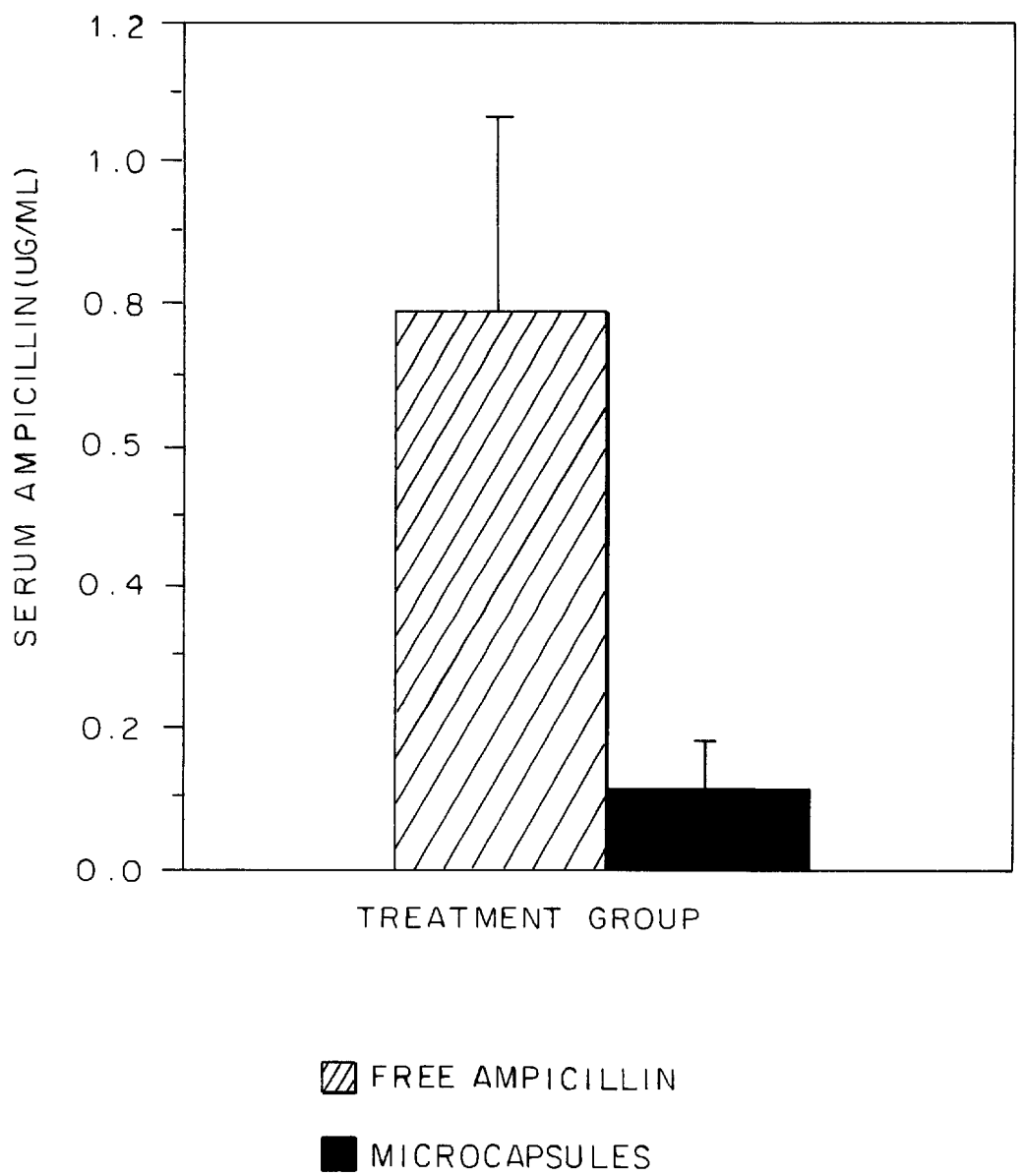
FIG. 5 shows mean serum levels of ampicillin at 1-hour following implantation of either microencapsulated ampicillin or unencapsulated ampicillin into the medullary canal of the rabbit tibia with experimental osteomyelitis.

In the final experiment, where local antibiotic therapy was delayed for 7 days and was institut ed in conjunction with debridement, a 100 animals treated w ith debridement plus microencapsulated ampicillin (Table 4). In contrast, of the 10 animals treated with debridement plus an equivalent dose of unencapsulated ampicillin powder, 70 seen in FIG. 5, at 1 hour after implantation of the antibiotics into the medullary canal, the mean serum concentration of ampicillin in the animals receiving unencapsulated ampicillin was approximately 7 times higher (0.79+024 micrograms/ml) than in the group that was treated with microencapsulated ampicillin anhydrate (0.11+0.08 micrograms/ml). This finding suggests that the free unencapsulated drug diffuses rapidly from the site of administration and does not remain localized for a sufficient time interval to eradicate the infection. The fact that 70 animals treated with the unencapsulated form of the drug developed osteomyelitis substantiates this conclusion. The ampicillin-loaded microcapsules/spheres, on the other hand, remain localized at the site of administration thereby continuing to release high concentrations of the antibiotic over time resulting in the elimination of the infecting organisms.

Applicants' experimental studies have demonstrated that a controlled-release and biodegradable antibiotic delivery system was successful for the eradication of a susceptible organism from an osteomyelitic focus when used in conjunction with adequate debridement.

Preparation of Ampicillin Anhydrate Microcapsules

EXAMPLE 8

About 500 g of a 10 wt alcohol) (PVA) was added to a 1-L (liter) resin kettle and cooled to 5° C. while being stirred at 650 rpm with a 2.5-in. Teflon turbine impeller driven by a motor and a control unit. A solution consisting of 5 g of 68:32 poly(DL-lactide-co-glycolide) in a mixture of 40 g of dichloromethane and 20 g of acetone was prepared in a separate container and stirred magnetically while in an ice bath. In still another container, 5 g of ampicillin anhydrate was dispersed in 15 g acetone. This mixture was stirred magnetically and then sonicated to achieve uniform dispersion of single ampicillin anhydrate crystals. After sonication, the container was placed in an ice bath, magnetic stirring was continued, and additional acetone was added to give a total of 30 g of acetone. After complete dissolution of the copolymer, the ampicillin-acetone dispersion was added to the copolymer solution. The resulting mixture was stirred magnetically in an ice bath for about 30 minutes or until homogeneous, and it was then added to the reaction flask containing the aqueous PVA solution. The stir rate was reduced from 650 to 500 rpm after the addition was complete. After 15 minutes, the pressure was reduced to 550 torr to begin slow evaporation of the organic solvent (dichloromethane and acetone). The pressure was further reduced to 250 torr. This pressure was maintained for another 18 to 24 hours. The flask was then opened, the suspension was removed, and the microcapsules were separated from the PVA solution by centrifugation. The microcapsules were then washed twice with water, centrifuged, and washed once more with water and recovered by filtration. The microcapsules were then dried in vacuo and separated into various size fractions by sieving. A free-flowing powder of spherical particles was obtained.

EXAMPLE 9

Dissolve 1.2 g of 50:50 poly(DL-lactide-co-glycolide) in 102 g of methylene chloride. Ampicillin anhydrate (0.8 g) is next added to the stirring copolymer solution. This mixture (dispersion of drug in the copolymer solution) is then placed in a 200-mL resin kettle equipped with a true bore stirrer having a 1.5-inch Teflon turbine impeller driven by a motor. While the mixture is stirring at 700 to 800 rpm, 48 mL of 100 centastoke (cSt) silicone oil is pumped into the resin kettle to cause the poly(DL-lactide-co-glycolide) to coacervate and coat the dispersed ampicillin anhydrate particles. After the silicone oil is added to the resin kettle, the contents of the kettle are poured into heptane to harden the microcapsules/spheres. After stirring in the heptane for 2 hours, the microcapsules/spheres are collected on a funnel an dried. A free-flowing powder of spherical different sized particles is obtained.

In Vitro Characterization of Microcapsules/Spheres

The core loadings of microcapsules/spheres comprising [$^{14}$C]-ampicillin anhydrate and DL-PLG were measured by liquid scintillation counting. The core loading of microcapsules/spheres consisting of unlabeled ampicillin anhydrate and some radiolabeled ampicillin anhydrate and DL-PLG was measured by using a microbial assay. In the former instance, microcapsules/spheres (about 15 mg) were solubilized in 1 mL of 0.5 N dimethyl dialkyl quaternary ammonium hydroxide in toluene (Soluene-350) at 55° C. for 2 to 4 hours. Then, 14 ml of scintillation cocktail (1,4-bis [2-(5-phenyloxazolyl] benzene (PPO/POPOP) in toluene) was added, and the radioactivity was measured with a liquid scintillation spectrometer. In the latter instance, microcapsules/spheres (about 15 mg) were placed in 5 mL of methylene chloride. Following dissolution of the DL-PLG excipient, the insoluble ampicillin anhydrate was extracted from the methylene chloride with four volumes of sterile 0.1 M potassium phosphate buffer (pH 8.0). These aqueous extracts were then assayed for the antibiotic using *Sarcina lutea* ATCC 9341 (American Tye Culture Collection, Rockville, Md.) and the agar-diffusion microbial assay previously described in the literature by Kavanagh, F. (ed.) Antibiotic Substances in Analytical Microbiology, Vol. II, 1972.

The in vitro release kinetics of [$^{14}$C]-ampicillin anhydrate microcapsules/spheres was determined following the placement of 30 mg of microcapsules in an 8-ounce bottle. The release study was initiated by the addition of 50 mL of receiving fluid consisting of 0.1 m potassium phosphate buffer (pH 7.4). The bottle was then sealed and placed in an oscillating (125 cycles/minutes) shaker bath maintained at 37° C. Periodically, a 3-ml aliquot of the receiving fluid was removed for assay and replaced with a fresh 3-ml aliquot of receiving fluid to maintain a constant volume of receiving fluid throughout the study. The 3-ml aliquots were assayed for drug by liquid scintillation counting using 12 ml Scinti Verse-I (Fisher Scientific Co., Pittsburgh, Pa.). The cumulative amount of the drug released into the receiving fluid was calculated.

The in vitro release kinetics of unlabeled ampicillin anhydrate microcapsules/spheres was determined in the following manner:

A known amount of ampicillin anhydrate microcapsules/spheres (about 4 mg of microencapsulated ampicillin anhydrate) and 5.0 ml of sterile receiving fluid (0.1 M potassium phosphate buffer, pH 7.4) were added into dialysis tubing. The ends of the tubing were sealed with plastic clamps. The clamped dialysis tubing containing the microcapsules/spheres were placed into a sterile 8-ounce bottle containing 100 ml of sterile receiving fluid (0.1 M potassium phosphate buffer, pH 7.4). The bottle was placed in a shaker bath maintained at 37° C. and shaked at 120 cycles per second with about 3-cm stroke. The receiving fluid was previously sterilized in an autoclave for 20 minutes at 121° C. Several dialysis tubing assemblies were prepared for one release study. At Days 1, 2, 4, 7, 10, 13, 15, 18, and 25, one assembly was removed from its receiving fluid and air dried.

After drying the assembly, all particles remaining inside the dialysis tubing were quantitatively transferred to a sterile, glass test tube (16 by 125 mm), 5 ml of methylene chloride were added to dissolve the microcapsules, and the drug was extracted with three 5-ml portions of sterile 0.1 M potassium phosphate buffer (pH 8.1). The extraction and preparation of the sample (along with controls) was performed using the procedures for core-loading analysis as discussed above in the extracted samples and controls using the microbiological assay. Knowing the amount of microencapsulated drug initially placed in the dialysis tubing and the amount of drug remaining in the dialysis tubing after incubation with receiving fluid, the amount of drug released was determined by calculating the difference between them.

In Vivo Release Profiles of Ampicillin from Microcansules/Spheres

The rate and duration of release of ampicillin anhydrate from the microcapsules/spheres were determined in vivo in rats. In one experiment, about 50- to 80-mg doses of microencapsulated and unencapsulated ampicillin anhydrate were sterilized in disposable syringes with a 2.0- or 2.5- Mrad dose of gamma radiation at dry-ice temperature. The sterile microcapsules/spheres and unencapsulated [$^{14}$C]- ampicillin anhydrate were then suspended in about 2.0 mL of an injection vehicle comprising 2 wt percent of commercially available carboxymethyl cellulose (Type 7LF, Hercules Inc., Wilmington, Del.) and 1 wt percent Tween 20 (ICI Americas Inc., Wilmington, Del.) in sterile water and autoclaved at 121° C. for 15 minutes. The microcapsules/ spheres were administered subcutaneously into the mid-back region of lightly anesthestized (ether), male Sprague-Dawley rats. The rats were fed standard laboratory food and water ad libidum and were housed in individual stainless steel cages fitted with metabolism funnels and screens that separated and collected the feces and urine. The urine from each rat was collected, weighed, and analyzed for [$^{14}$C]- content by liquid scintillation counting. The actual doses of microcapsules/spheres or unencapsulated drug administered to each rat was determined after injection by measuring the amount of drug residue in each syringe by liquid scintillation counting. The amount of radioactivity excreted daily by each rat was normalized by the dose of microencapsulated or unencapsulated ampicillin anhydrate that each rat actually received. This result was then plotted as a function of time.

In a second experiment, unlabelled ampicillin anhydrate microcapsules/spheres were tested in rats. The rats were administered the microcapsules/spheres in the same manner as that described in the first experiment. The microbiological assay described above was used to determine the amount of ampicillin in the serum of these rats.

In Vivo Efficacy Evaluation of Microcapsules/ Spheres

Experiments to evaluate the efficacy of prototype microcapsules/spheres in vivo were performed in 250- to 300-g male, Walter Reed strain, albino rats that were anesthetized with sodium pentobarbital. The right hind leg was razor-shaved, scrubbed with Betadine (The Purdue Frederick Co., Norwalk, Conn.), and swabbed with 70 length and 1 cm deep was made in the thigh muscle and contaminated with 0.2 g of sterile dirt. The muscles were traumatized by uniformly pinching them with tissue forceps, and then the wounds were inoculated with known quantities of *Staphylococcus aureus* ATCC 6538P and *Streptococcus pyogenes* ATCC 19615. All rats were inoculated on the same day of the experiment with the same quantitated bacterial suspension to insure uniform inoculum in all wounds. The artificially contaminated wounds were treated within 1 hour by layering sterile, pre-weighed amounts of microencapsulated antibiotic directly on the wounds. Control groups consisted of animals with wounds that either received no therapy, were overlaid with placebo (unloaded) microcapsules/spheres, or were treated with locally applied, powdered unencapsulated ampicillin anhydrate. Following treatment, all wounds were sutured closed with 3-0 black silk.

Three groups of 20 rats each were used in an efficacy experiment to evaluate Mmicrocapsules/spheres A382-140-1 formulated from 70:30 DL-PLG. In this experiment, a group of animals with wounds overlaid with 0.5 g of unloaded microcapsules/spheres was substituted for the untreated (no therapy) group evaluated in each succeeding dose-response experiment. In addition, a group of 20 rats treated with 0.5 g of ampicillin anhydrate microcapsules/spheres per wound, and a group of 20 rats treated with 120 mg of locally applied uncapsulated ampicillin anhydrate powder per wound were evaluated. Five animals from each group were sacrificed at 2, 6, 8, and 14 days and evaluated for the presence of ampicillin in the serum and tissue and for the presence of infection.

Two dose-response experiments were performed in which Microcapsules/spheres A681-31-1, formulated from 70:30 DL-PLG, and Microcapsules/spheres B213-66-1S, formulated from 53:47 DL-PLG were evaluated. Seven groups of 15 rats each were treated with the doses of microcapsules shown in Table I. Each experiment included an additional group of 15 rats which remained untreated.

In dose-response Experiment I, five animals from each group were sacrificed at 2, 7, and 14 days and evaluated for ampicillin levels and number of bacteria present per gram of tissue at each wound site. Serum ampicillin levels were assayed at 2, 4, 7, and 14 days. In dose-response Experiment II, five animals from each group were sacrificed at 7, 14, and 21 days and evaluated for ampicillin levels and number of bacteria present per gram of tissue. Serum ampicillin levels were determined at 2, 7, 14, and 21 days.

Microcapsules/spheres in a 45 to 106 micron size range made by the phase-separation process were evaluated in these experiments. The ampicillin anhydrate content of the microcapsules/spheres (core loading), batch number, and ampicillin anhydrate equivalent for each dose of microcapsules/spheres are shown in Table 1.

In all experiments, bacterial counts were performed on homogenized, preweighed tissue that had been aseptically removed from the wound sites. Serial dilutions of the homogenized tissue specimens were plated on sheep blood agar. Colonies of *Staphylococcus aureus* could be easily differentiated from *Streptococcus pyogenes* on the basis of colonial morphology. Tissue from varying distances around the wound site and serum removed by cardiac puncture were assayed for antibiotic content. This was accomplished by placing discs saturated with known quantities of serum or tissue homogenates on the surface of Mueller-Hinton agar which had been previously seeded with standardized amounts of *Sarcina lutea* ATCC 9341. Following incubation at 37° C., inhibition zones were measured. Freshly diluted stock solutions containing known quantities of ampicillin anhydrate served as standards. Diameters of the inhibition zones were converted to antibiotic concentrations using standard curves generated by plotting the logarithm of the drug concentration against the zone diameters.

TEST RESULTS

Microcapsule/Spheres In Vitro Evaluation

Ampicillin anhydrate was microencapsulated with DL-PLG excipient. DL-PLG is a biocompatible aliphatic polyester that undergoes random, nonenzymatic, hydrolytic scission of the ester linkages under physiological conditions to form lactic acid and glycolic acid. These hydrolysis products are readily metabolized. The purpose of the DL-PLG is to control the release of the ampicillin anhydrate from the antibiotic microcapsule/spheres formulation and to protect the reservoir of ampicillin anhydrate from degradation before it is released from the microcapsules/spheres. Two DL-PLG excipients were used in this study. One DL-PLG had a lactide-to-glycolide mole ratio of 70:30 and the other, 53:47. The 53:47 DL-PLG biodegrades faster than the 70:30 DL-PLG because of its higher glycolide content.

A phase-separation microencapsulation process afforded microcapsules/spheres in yields of better than 95. The microencapsulated ampicillin anhydrated product was a fine, free-flowing powder. The microcapsules/spheres are relatively spherical in shape, but have puckered regions. Although these puckered regions exist, the polymer coating was continuous, and there was no evidence of any fractures or pinholes on the surfaces of the microcapsules. Moreover, the photomicrograph obtained by scanning electron microscopy of ampicillin anhydrate microcapsules did not show any evidence of free unencapsulated ampicillin anhydrate crystals either among the microcapsules or protruding through the surface of the microcapsules.

The drug content (core loading) of the ampicillin anhydrate microcapsule/sphere formations was measured to assess how much ampicillin anhydrate was incorporated in the microcapsules and to determine the bioactivity of the ampicillin anhydrate after it had been microencapsulated.

In general, the core loading of the 45-to $10^6$ microns size fraction was similar to the theoretical core loading. The core loading of a few batches of [$^{14}$C]-ampicillin anhydrate microcapsules/spheres was determined by microbial assay as well as by radioassay. Within experimental error, both assays gave similar results. This indicates that the ampicillin anhydrate was not inactivated during the microencapsulation process. Also, the core loading of ampicillin anhydrate microcapsules/spheres was determined by the microbial assay to determine the effect of 2.5 Mrad of gamma radiation on the microencapsulated drug. The radiation did not inactivate the drug because the core loading remained the same. For instance, 19.3 spheres with 70:30 DL-PLG assayed as 19.0 irradiation and 11.0 DL-PLG assayed as 11.4 irradiated unencapsulated and microencapsulated drug were also checked by thin layer chromatography. Irradiated and non-irradiated samples chromatographed the same, again indicating that no degradation of the drug was caused by gamma radiation at a dose of 2.5 Mrad.

Figure 1:
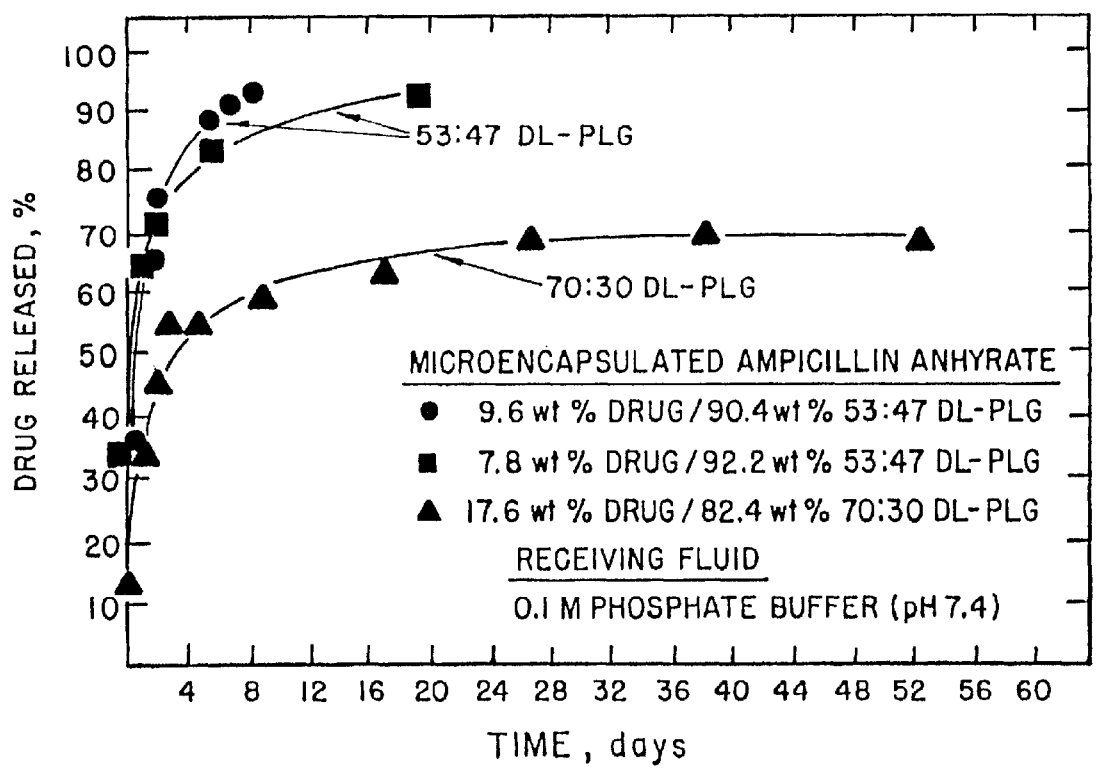
Figure 2:
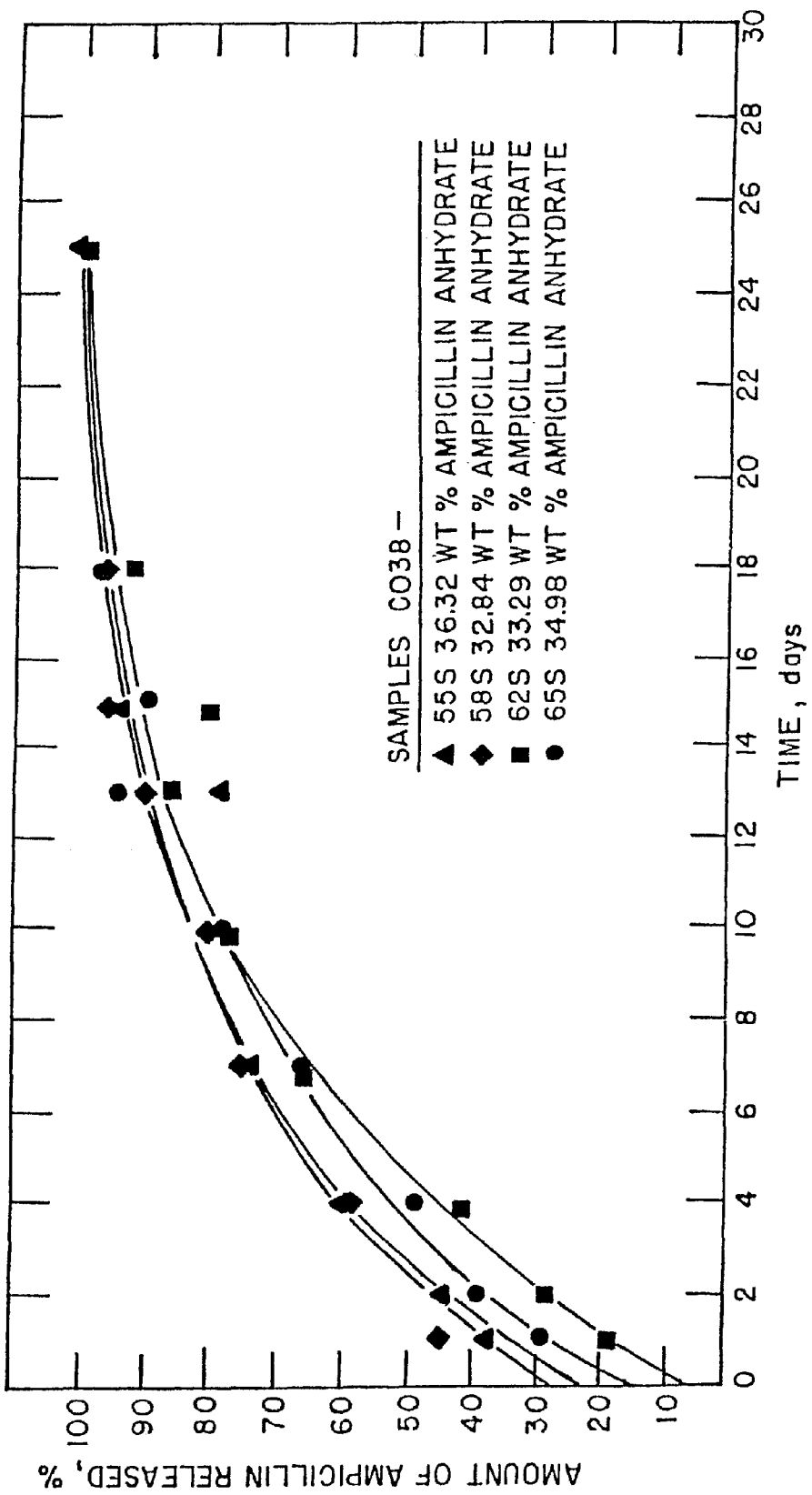
FIG. 2 shows the in vitro release of [$^{14}$C]-ampicillin anhydrate from sterilized microcapsules (10 to 100 micrometers consisting of about 35 weight percent ampicillin and about 65 weight percent of 53:47 DL-PLG polymer.

In vitro release measurements were used to identify an ampicillin anhydrate microcapsule/sphere formulation that would release all of its drug at a controlled rate over a period of two weeks. The formulation that displayed the desired in vitro release kinetics were microcapsules/spheres with diameters of 45 to 106 microns consisting of about 10 wt percent ampicillin anhydrate (Bristol Laboratories, Syracuse, N.Y.) and microcapsules/spheres with diameters of 10 to 100 microns consisting of about 35 wt percent ampicillin anhydrate (Wyeth Laboratories, West Chester, Pa.) and about 65 wt percent 53:47 DL-PLG. FIGS. 1 and 2 show the in vitro release profiles of two samples of these prototype microcapsules. The microcapsules released a desirable initial burst of drug, representing about 30. The remaining drug was then released at a slower controlled rate.

The in vitro release profile of sterilized (2.5 Mrad), 17.6 compared with the release profiles of sterilized (2.0 Mrad), 9.6 and 7.8 DL-PLG (FIG. 1).

Microcapsule/Sphere In Vivo Evaluation

Figure 3:
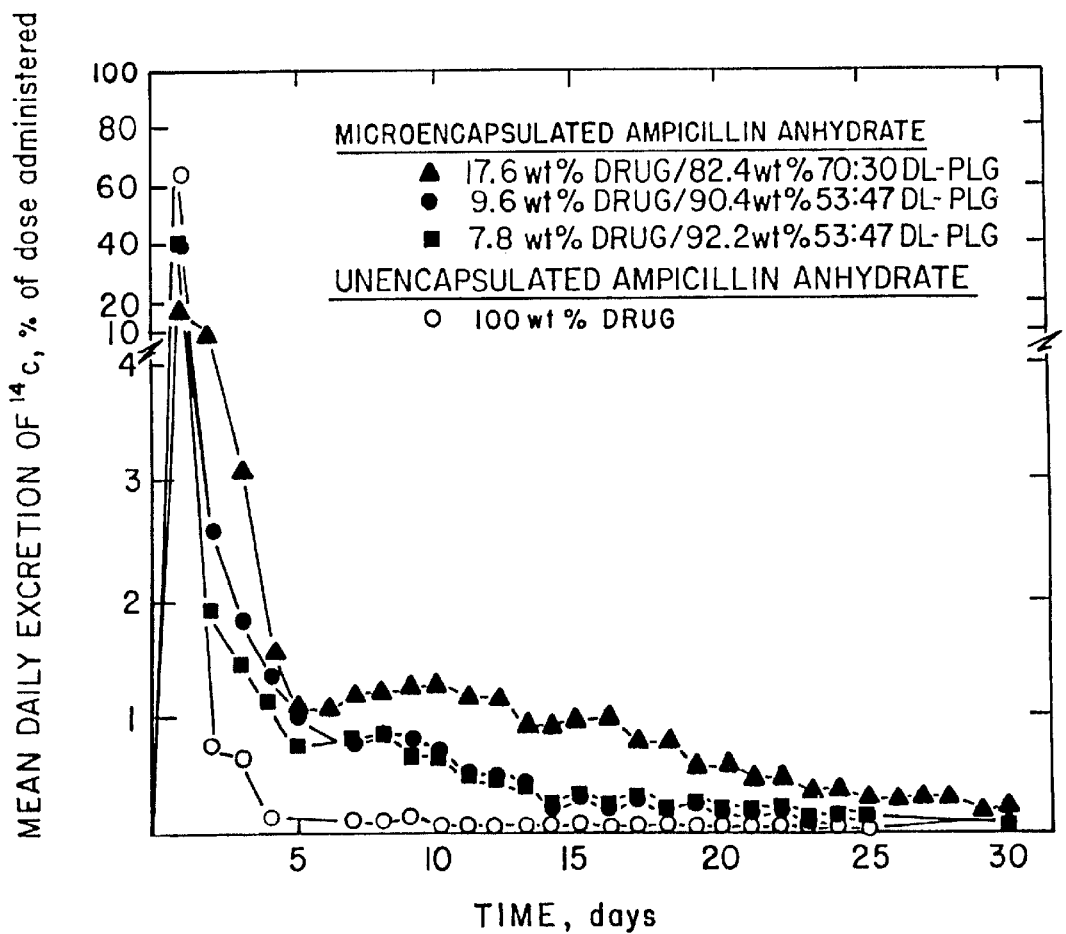
FIG. 3 shows the mean daily excretion of [$^{14}$C] from rats receiving subcutaneous injections of sterilized microencapsulated and unencapsulated [$^{14}$C]-ampicillin anhydrate.
Figure 4:
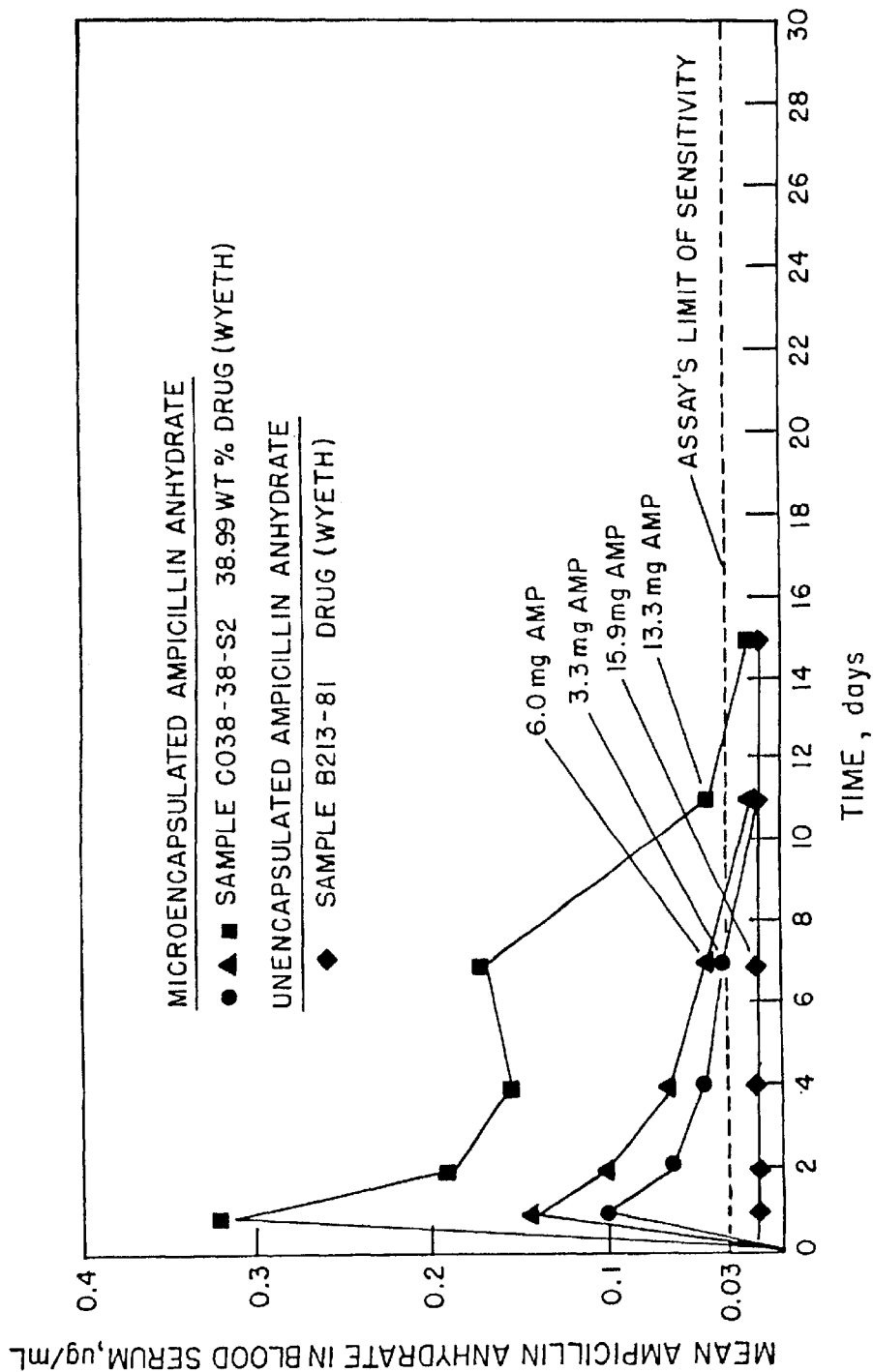
FIG. 4 illustrates that encapsulated as well as the ampicillin anhydrate showed a fast release of drug during Day 1. By Day 4, the amount of ampicillin found in the serum of animals dosed with the unencapsulated drug was below the level of detection of the assay, whereas serum levels of ampicillin were dectable in animals receiving encapsulated ampicillin for up to 11 days.

Pharmacokinetic studies were performed with unencapsulated ampicillin anhydrate and the same samples of microcapsules that were tested in vitro, as previously described. As shown in FIGS. 3 and 4, the unencapsulated drug as well as the microcapsules/spheres showed a fast release of drug during Day 1. By Day 4, the amount of ampicillin found in the urine or serum of animals dosed with the unencapsulated drug was below the level of detection of the assay. On the other hand, the microcapsule/sphere formulations maintained an elevated level of drug in the urine or serum for extended periods. Both samples of microcapsules/spheres made with the 53:47 DL-PLG had similar release profiles and released drug for about two weeks. As illustrated in FIG. 3, the microcapsules/spheres prepared with 70:30 DL-PLG released drug for at least four weeks. The results of these pharmacokinetic studies corroborate results of the in vivo release studies described. The 53:47 microcapsules/spheres closely meet the desired target duration of release of two weeks.

The slow rate of ampicillin release from the 70:30 microcapsules/spheres, as shown in FIG. 3, may be undesirable because a low level of ampicillin anhydrate released over a long period may provide favorable conditions for the development of drug-resistant bacterial strains. This slower release of drug could be attributed to the slower biodegradation rate of the 70:30 DL-PLG, where the water-soluble ampicillin anhydrate remained trapped inside the hydrophobic DL-PLG excipient until the excipient biodegraded completely. More specifically, for microcapsules/spheres prepared with either the 70:30 or 53:47 DL-PLG, one could speculate that the release of drug is due to diffusion of the drug through water-filled pores, pores that enlarge as more and more drug is released and as the DL-PLG bioerodes.

However, all ampicillin anhydrate microcapsules/spheres formulated effectively reduced bacterial counts in contaminated wounds. The most dramatic observation was the rapid elimination of *Streptococcus pyogenes*. *Streptococcus pyogenes* was present in 90 from microcapsule/sphere-treated wounds within 48 hours. All three of the microcapsule/sphere batches evaluated were equally successful in eliminating this organism within two days. At 7 days *Staphylococcus aureus* remained in all treated wounds; however, compared to untreated controls, the bacterial count per gram of tissue decreased by at least 2 $\log_{10}$ between Days 2 and 7. This reduction was not observed in untreated controls. In the efficacy evaluation of microcapsules/spheres A382-140-1, wounds treated with unloaded DL-PLG microcapsules, as well as those treated with topical unencapsulated ampicillin anhydrate, remained infected at 14 days with>$10^5$ organisms per gram of tissue; whereas, 60 ampicillin anhydrate were sterile. The wounds of the remaining $4010^3$ organisms per gram of tissue. By 14 days, regardless of the dose administered (0.5–0.05 g), all wounds treated with microcapsule/sphere sample A681-31-1 were sterile; whereas, all untreated wounds remained infected with>$10^5$ organisms per gram of tissue. At 14 days, all wounds treated with 0.15 g of microcapsules/spheres B213-66-1S were sterile, however, $5.7 \times 10^2$ *Staphylococcus aureus* per gram of tissue were counted in the wounds of one animal treated with a 0.25-g dose of encapsulated ampicillin anhydrate. This failure was attributed to an abscess around a suture on the wound surface. All wounds treated with 0.15 g of microcapsules/spheres (B213-66-1S) were sterile; however, in the group treated with a 0.05-g dose of microcapsules/spheres, one wound remained contaminated with $3.6 \times 10^4$ *Staphylococcus aureus* per gram of tissue. The untreated control animals, evaluated in parallel with the microcapsule/sphere-treated groups, averaged $1.4 \times 10^5$, *Staphylococcus aureus* per gram of tissue.

Serum levels of drug were dependent upon the ampicillin anhydrate reservoir present inside the microcapsules/spheres (core loading), the dose, and the ampicillin release characteristics. Administration of 0.25 g of Microcapsules/spheres A681-31-1, which contained a 45.25 mg ampicillin reservoir per wound, maintained a serum ampicillin level of 8.0±7.3 microgram/milliliter for up to 4 days post-treatment. A dose twice that amount (90.50 mg ampicillin equivalent) maintained detectable serum ampicillin for up to 7 days post-treatment at a serum ampicillin concentration of 15.95±5.0 microgram/milliliter for the first 4 days. Serum ampicillin was not detected in animals whose wounds were treated with microcapsule/sphere doses containing an ampicillin equivalent of 28.50 mg or less. Even though serum ampicillin was not detected in any animal at 14 days, the tissue levels at this time were above the minimal inhibitory concentrations required to kill both infecting organisms in all animals treated with microencapsulated ampicillin anhydrate. This was true with microcapsule/sphere doses as low as 0.05 gram per wound. Even though serum ampicillin was not detected, microbial bioassay for ampicillin in tissue removed from wounds treated with 0.05 gram of microcapsules/spheres (A681-31-1) contained a mean (n=5) ampicillin level of 54, 70, and 21 micrograms/gram of tissue at 2, 7, and 14 days, respectively. Because the minimal inhibitory concentrations of ampicillin required to kill 95 of *Staphylococcus aureus* and 97 *pyogenes* is 0.5 and 0.05 micrograms/milliliter, respectively, it is a reasonable assumption that a more than adequate therapeutic amount of drug was present at the wound site throughout the two-week treatment period.

In vitro release studies performed on microcapsules/spheres formulated with 70:30 DL-PLG (A382-140-1 and A681-31-1) showed drug release at an efficacious rate over two weeks, but also at a slower rate for an additional 50 days. The continued release of low amounts of antibiotic in wounds after two to three weeks is undesirable because of the potential to provide favorable conditions for the emergence of ampicillin resistant organisms in wounds which might harbor small numbers or bacteria. Therefore, to reduce or eliminate drug trailing, microcapsules/spheres were reformulated by encapsulating ampicillin anhydrate within the faster biodegrading polymer 53:47, DL-PLG (sample B213-66-1S), in vitro release profiles showed a release of 85 to 92 within two weeks. On the seventh day following treatment of wounds with 0.15 gram of Microcapsules/spheres B213-66-1S, a mean (n=5) of 162.5 g of ampicillin per gram of tissue was quantitated. In vitro release studies suggest that this amount drops rapidly in the second week so that by 14 days marginal killing concentrations are present. In vivo analysis of tissue removed from wounds treated 15 days previously with 0.25 gram of these microcapsules/spheres contained<1.9 micrograms/gram of ampicillin per gram. Although <0.22 micrograms/gram of ampicillin was detected in wounds treated with 0.15 gram, it was unusual to detect any ampicillin at 14 days in tissue from wounds treated with 0.05 gram per wound. At 21 days post-treatment, ampicillin was not detected in any of the wounds.

No serum levels of ampicillin were detected in any of the rats treated with Microcapsules/spheres B213-66-1S. This was expected because lower doses (ampicillin equivalent) were administered. (Table 1).

B. Cefazolin (CZ) microspheres. The CZ microspheres used in these studies were produced by Southern Research Institute, Birmingham, Ala. The microspheres consisted of 77.8 weight % copolymer (50:50 molar ratio of lactide to glycolide) with a core leading dose of 22.2 weight % cefazolin. The size of the microspheres ranged from 90 to 355 um in diameter and they were sterilized with 2.7 Mrad of gamma radiation. In vitro release kinetic studies showed that approximately 20% of the cefazolin was released from the microspheres within 6 hours, with the remainder of antibiotic release extending over a period of 15 days.

Rat wound infection model. Experimental wounds were surgically created in the paraspinous muscles of Sprague-Dawley rats following induction of anesthesia with ketamine and xylazine. Sterile sand (100 mg) was implanted into the wound site to simulate a foreign body and the wounds were inoculated with $5 \times 10^6$ CFU each of *Staphylococcus aureus* ATCC 27660 and *Escherichia coli* ATCC 25922. The minimum inhibitory concentration (MIC) of cefazolin for each of these organisms was 4 ug/ml and 2 ug/ml, respectively. The animals were then randomly distributed in 6 groups. Groups A, B, and C (6 rats per group) received local antibiotic therapy with 50 mg, 250 mg, or 500 mg of CZ microspheres, respectively. The microspheres were applied directly to the wounds and care was taken to achieve a relatively uniform distribution of the drug throughout the wound site. Group D (6 rats) received local antibiotic therapy with 110 mg of CZ powder. This dose was equivalent to the core-loading dose of cefazolin contained in 500 mg of CZ microspheres used to treat the Group C animals. Group E (6 rats) received systemic antibiotic therapy with cefazolin (30 mg/kg) which was administered as a single intramuscular bolus immediately after bacterial contamination of the wounds. Group F (3 rats) served as controls and received no antibiotic therapy. The wounds were then closed with surgical staples and the animals were returned to their cages. On postoperative day # 28, the rats were euthanized and tissue was obtained from each wound for quantitation of surviving bacteria. The tissue was weighed, homogenized, and serial 10-fold dilutions were prepared and plated on blood agar. The number of bacteria recovered from each wound was quantitated and expressed as CFFU/g tissue.

Rabbit fracture-fixation model. This study was conducted in two phases and was designed to evaluate the effect of early as well as delayed local antibiotic therapy for the prevention of infection in experimental fractures. In Phase I, open fractures were created in the right tibiae of New Zealand White rabbits after induction of anesthesia with ketamine and xylazine. The fractures were then inoculated with 0.5 ml of *S. aureus* ATCC 27660 ($2.0 \times 10^7$ CFU/ml). Within 30 minutes following bacterial contamination, the animals were randomly distributed in 5 groups. Group A (8 rabbits) received local antibiotic therapy with 300 mg of cefazolin microspheres which was applied directly to the fracture site and the deep musculature. Group B (8 rabbits) received local antibiotic therapy with an equivalent dose of CZ powder. Group C (8 rabbits) received systemic antibiotic therapy with cefazolin (25 mg/kg/day) for 7 days. Groups D and E (4 rabbits per group) served as controls and received either local application of placebo microspheres (without cefazolin) or no treatment, respectively. The fractures were then reduced and plated with a 4-hole dynamic compression plate. Immediately prior to wound closure, animals in Groups A and B received an additional dose of either CZ microspheres (300 mg) or an equivalent dose of CZ powder, respectively, which was applied directly over the fixation plates and the periosteal tissue. The wounds were then repaired with sutures and the animals were returned to their cages. Blood was obtained within 1 hour and again at 24 hours after treatment from all Group A and B animals for quantitation of serum cefazolin levels which was measured by a microbial inhibition bioassay[9]. Eight weeks later, all surviving animals were euthanized and the tibiae were harvested for bacteriological analysis, the bones were crushed to small pieces with sterile mortar and pestle and saline was added to make a particulate suspension. Serial dilutions were then prepared and streaked on blood agar for bacterial isolation. The number of *S. aureus* colonies recovered from each specimen was quantitated and expressed as CFU/g of bone.

In Phase II, fractures were created in the right tibia of 29 rabbits and contaminated with *S. aureus* as described above. After a 2 hour delay, the animals were randomly distributed in 3 groups. Group A (10 rabbits) received local antibiotic therapy with 600 mg of CZ microspheres. Group B (10 rabbits) received local antibiotic therapy with an equivalent dose of CZ powder. Group C (9 rabbits) served as controls and received no treatment. The fractures were then reduced, plated, and the wounds were closed with sutures. Eight weeks later, the surviving animals were euthanized and the tibiae were harvested and processed for isolation of bacteria as described above.

Results

Rat wound infection model. Table 5 shows the effect of local versus systemic cefazolin therapy on the contamination rate in rat soft-tissue wounds at 28 days postinfection. Local antibiotic therapy with CZ microspheres, in doses ranging from 50 to 500 mg per wound, was highly effective for eliminating both organisms from the wounds. The maximum effect was achieved in the Group C animals who received the highest dose of CZ microspheres (500 mg) where *E. coli* and *S. aureus* were eliminated from 100% of the wounds. Even at the lowest dose used (50 mg/wound), 4 of 6 wounds were rendered completely sterile. Local antibiotic therapy with free CZ powder sterilized the wounds in 5 of 6 (83%) animals. In contrast, systemic administration of cefazolin (30 mg/kg) failed to sterilize the wounds in any of the 6 Group E animals tested.

Rabbit fracture-fixation model. Table 6 shows the results of the clinical and bacteriological findings at 8 weeks in 25 surviving rabbits when local or systemic antibiotic therapy with cefazolin was initiated within 30 minutes following bacterial contamination of the fractures. Deep infection, defined as the presence of pus on the fixation plate or in the deep tissues, was noted in 6 of the 7 (86%) control animals in Group D (placebo microspheres) and group E (no treatment). Cultures of the tibiae from all 7 controls were positive for *S. aureus*. Of the 5 surviving Group animals who received a 1 week course of systemic cefazolin therapy, deep infection was noted in 3 cases and *S. aureus* was recovered from the bones of 4 of the 5 animals. In contrast, no clinical evidence of infection was detected in any of the 7 Group A animals who received an equivalent local dose of free CZ powder. Cultures of the tibiae were sterile in 6 of (86%) Group A and 5 of 6 (83%) Group B animals, respectively. There was a statistically significant difference in the mean log *S. aureus* counts of the Group A and Group B animals and all other groups by analysis of variance (p <0.05). The mean log *S. aureus* counts for Group C was also significantly different from all groups with the exception of Group E (no treatment).

Table 7 shows the results of the clinical and bacteriological findings at 8 weeks in 23 surviving rabbits when local antibiotic therapy was delayed for 2 hours following bacterial contamination of the fractures. Clinical evidence of infection was present in 5 of 7 (71% control animals in Group C and cultures of the tibiae yielded *S. aureus* in all 7 cases. Of the 8 animals in Group B who received local antibiotic therapy with Cz powder, deep infection was noted in 4 animals and *S. aureus* was received in 6 of 8 (75%) cases. In contrast, none of the 8 animals in Group Aa (CZ microspheres) developed clinical infections and cultures of the tibiae were sterile in all cases. One way analysis of variance showed a statistically significant difference in the mean log *S. aureus* counts between Groups A and B (p=0.0014); Groups A and C (p<0.0001); and Groups B and C (p=0.0269).

TABLE 1

Ampicillin Anhydrate Microcapsules Evaluated in Rats

| In Vivo Experiment | Microcapsule Batch | Antibiotic Core Loading, Wt Percent | Microcapsule Dose/ Wound, g (Antibiotic Equivalent, mg) |
|---|---|---|---|
| Efficacy | A382-140-1 | 18.5 | 0.50 (92.50) |
| Dose-Response I | A681-31-1 | 18.1 | 0.50 (90.50) |
| | | | 0.25 (45.25) |
| | | | 0.10 (18.10) |
| | | | 0.05 (9.05) |
| Dose-Response II | B213-66-1S | 11.4 | 0.25 (28.50) |
| | | | 0.15 (17.10) |
| | | | 0.05 (5.70) |

TABLE 2

Effect of Immediate Antibiotic Therapy for Prevention of Experimental Osteomyelitis in a Rabbit Tibia Model

| Group Bacterial Counts[b] | Treatment | Radiographic Severity[a] | Positive Bone Cultures |
|---|---|---|---|
| A 0 | Parenteral therapy for 14 days | 0 | 0/6 |
| B 0 | Microencapsulated ampicillin[c] | 0.43 ± 1.13 | 0/7 |
| C 1.2(±2.3) × 10$^2$ | Unencapsulated ampicillin[c] | 0 | 1/4 |
| D 4.9(±8.3) × 10$^6$ | Placebo microcapsules[c] | 7.00 ± 0.0 | 4/4 |
| E 1.3(±0.7) × 10$^6$ | Injection vehicle[c] | 6.67 ± 0.58 | 4/4 |
| F 2.0(±4.5) × 10$^7$ | No treatment | 5.25 ± 2.06 | 5/5 |

[a]Mean radiographic severity score at 7-weeks post treatment.
[b]Mean (± standard deviation) CFU of *S. aureus* recovered per gram of bone.
[c]Intramedullary injection.

TABLE 3

Effect of Delayed Therapy without Debridement for Treatment of Experimental Osteomyelitis in a Rabbit Tibia Model

| Group | Treatment | Positive Bone Cultures | Bacterial Counts[b] |
|---|---|---|---|
| A | Parenteral therapy for 14 days | 6/8 | 5.9(±16.7) × 10$^6$ |
| B | Microencapsulated ampicillin[c] | 4/8 | 1.2(±2.2) × 10$^3$ |
| C | Unencapsulated ampicillin[c] | 5/7 | 2.6(±7.0) × 10$^5$ |
| D | No treatment | 6/6 | 2.8(±2.9) × 10$^5$ |

[a]No statistically significant differences between groups by Chi square analysis (p = 0.23)
[b]Mean (± standard deviation) CFU of *S. aureus* recovered per gram of bone.
[c]Intramedullary injection.

TABLE 4

Effect of Delayed Therapy with Debridement for Treatment of Experimental Osteomyelitis in a Rabbit Tibia Model

| Group | Treatment | Positive Bone Cultures | Bacterial Counts[b] |
|---|---|---|---|
| A | Microencapsulated ampicillin | 0/10[c] | 0 |
| B | Unencapsulated ampicillin | 7/10 | 3.3(±4.8) × 10$^2$ |
| C | Placebo microcapsules | 5/5 | 9.1(±10.9) × 10$^4$ |
| D | Injection vehicle | 5/5 | 3.7(±4.9) × 10$^5$ |

[a]All substances were implanted locally into the medullary canal at the time of debridement.
[b]Mean (± standard deviation) CFU of *S. aureus* recovered per gram of bone.
[c]Significantly different (p < 0.01) from all other groups by Chi square analysis.

TABLE 5

Survival of *E. coli* and *S. aureus* in rat soft-tissue at 28 days following local or systemic treatment with cefazolin.

| Treatment Group (N) | Dose | Mean (±sd) Log CFU/g tissue *E. coli* | Mean (±sd) Log CFU/g tissue *S. aureus* | Contamination Rate |
|---|---|---|---|---|
| A: CZ microspheres (6) | 50 mg | 1.01 ± 1.59 | 0.50 ± 1.21 | 2/6 (33%) |
| B: CZ microspheres (6) | 250 mg | 0.91 ± 1.41 | 0.42 ± 1.04 | 2/6 (33%) |
| C: CZ microspheres (6) | 500 mg | 0 | 0 | 0/6 (0%) |
| D: Free CZ powder (6) | 110 mg | 0.57 ± 1.40 | 0.53 ± 1.29 | 1/6 (17%) |
| E: Systemic C2 (6) | 30 mg/kg | 4.44 ± 0.51 | 0.83 ± 2.03 | 6/6 (100%) |
| F: No treatment (3) | 0 | 4.28 ± 0.34 | 2.12 ± 1.83 | 3/3 (100%) |

TABLE 6

Effect of early antibiotic therapy on infection in *S. aureus* contaminated rabbit tibial fractures stabilized with internal fixation.

| Treatment Group (N) | No. of Animals with: Deep Infection | No. of Animals with: Positive Bone Cultures | Mean (±SD) log bacteria (CFU/g) |
|---|---|---|---|
| A: CZ microspheres (7) | 0/7 | 1/7 | 0.3 ± 0.9 |
| B. CZ powder (6) | 0/6 | 1/6 | 0.2 ± 0.5 |
| C. Systemic CZ (5) | 3/5 | 4/5 | 3.0 ± 2.1 |
| D. Placebo microspheres (3) | 3/3 | 3/3 | 5.2 ± 0.2 |
| E. No treatment (4) | 3/4 | 4/4 | 4.2 ± 0.5 |

TABLE 7

Effect of delayed antibiotic therapy on infection rates in *S. aureus* contaminated rabbit tibial fractures.

| Treatment Group (N) | No. of Animals with: Deep Infection | No. of Animals with: Positive Bone Cultures | Mean (±SD) log bacteria (CFU/g) |
|---|---|---|---|
| A: CZ microspheres (8) | 0/8 | 0/8 | 0 |
| B. CZ powder (8) | 4/8 | 6/8 | 2.4 ± 1.6 |
| E. No treatment (7) | 5/7 | 7/7 | 4.3 ± 1.0 |

TABLE 8

Efficacy of Cefazolin Microspheres in Rat Soft
Tissue Wounds Contaiminated with a Cefazoll-Resistant Strain
of S. aureus (MIC = 64 μg/ml)

| Treatment Group | Dose | Number of Animals | Number (%) Sterile Wounds |
|---|---|---|---|
| CZ microspheres | 500 mg[a] | 6 | 5/6 (83%) |
| Free CZ powder | 110 mg | 6 | 6/6 (100%) |
| Systemic CZ | 30 mg/kg × 7 days | 6 | 0/6 (0%) |
| Controls | No antibiotics | 3[b] | 2/2 (0%) |

[a]500 mg of CZ microspheres was applied to the wounds representing 110 mg of cefazolin equivalent
[b]One control animal died during the experiment and no cultures were performed.
LEGEND:
CZ microspheres = Cefazolin-loaded lactide-co-glycolide microspheres
Free CZ powder = Unencapsulated cefazolin powder
Systemic CZ = Intramuscular administration of cefazolin (30 mg/kg/day) given at 8 hour intervals for 7 consecutive days.
Controls = No antibiotic treatment.

References
1. E. Jacob and J. A. Setterstrom, Milit. Med. 154, 311 (1981).
2. E. Jacob, J. M. Erpelding, and K. P. Murphy, Milit. Med. 157, 552 (1992).
3. R. S. Klein, S. A. Berger, and P. Yekutiel, Ann. Surg. 182, 15 (1975).
4. R. D. Livingston, Milit. Med. 150, 72 (1985).
5. T. H. Witschi and G. E. Omer, J. Trauma 10, 105 (1970).
6. M. Seidenstein and A. Newman, Arch. Surg. 96, 176 (1968).
7. E. Simchen and T. Sachs, Ann. surg. 182, 754 (1975).
8. J. A. Setterstrom et al., in Recent Advances in Drug Delivery Systems, S. W. Kim, Ed., (Plenum, N.Y., 1984), pp. 185–198.
9. J. V. Bennett, J. L. Brodei, E. J. Benner, and W. NM. Kirby, Appl. Microbiol. 14, 170 (1966).
10. H. E. Noyes, N. H. Chi, and L. T. Link, Milit. Med. 132, 461 (1967).
11. C. Heisterkamp, J. Vernick, R. L. Simmons, and T. Matsumoto, Milit. Med. 134, 13 (1969).

Applicants have developed microencapsulated antibiotics for the local treatment of contaiminated surgical and traumatic wounds. Preliminary studies have shown that local application of biodegradable antibiotic microspheres to experimental wounds that were contaiminated with resistant bacteria was extremely effective for prevention of wound infection. This success is attributed to the significantly higher local tissue antibiotic levels that can be achieved at the wound site with direct local application of microencapsulated antibiotics as compared to conventional systemic antibiotic dosing. The findings of the experimental studies are summarized below:

1. Ampicillin microspheres effectively prevented infection in 8/11 (73%) animals whose wounds were inoculated with an ampicillin-resistant strain of s. aureus (MIC=750 ug/ml). Systemic ampicillin failed in 9/9 (100%) cases.

2. Cefazolin microspheres effectively prevented infection in 5/6 (83%) animals whose wounds were inoculated with a methicillin-resistant strain of *S. aureus* which was also resistant to cefazolin (MIC=64 ug/ml). Systemic cefazolin failed in 5/6 (83%) cases.

3. It is preferred that a initial release (burst) of the encapsulated antibiotic occur within the first day and the remaining antibiotic be released over the next 2 to 3 weeks.

EXPERIMENTAL DESIGN FOR RAT SOFT-TISSUE WOUND INFECTION MODEL

Experimental surgical wounds were created in the paraspinous muscle of anesthetized Sprague Dawley rats, each weighing between 450 to 550 grams. The wounds were then contaiminated with 100 mg of sterile sand as an infection-potentiating agent. The wounds were then inoculated with $5 \times 10^6$ CFU of *S. aureus* ATCC 33593. This is a methicillin-resistant strain of *S. aureus* which is also resistant to cefazolin (MIC=64 ug/ml). The animals were then assigned to the following treatment groups:

Group A (n=6): 500 mg of cefazolin (CZ) microspheres was applied directly to the wounds. This dose contained 110 mg of cefazolin equivalent.

Group B (n=6): 110 mg of free CZ powder was applied directly to the wounds.

Group C (n=6): This group received intramuscular injections of CZ (30 mg/kg/day) at 8 hour intervals for 7 consecutive days.

Group D (n=3): This group served as controls and did not receive any antibiotic therapy.

The wounds were then closed with surgical staples and the animals were returned to their cages for the next 5 weeks. At that time, the animals were humanely euthanized and tissue was removed from the wounds and cultured for the presence of bacteria. The bacteriological data are presented in Table 8.

IX. UTILITY

Successful controlled release of bioactive ampicillin anhydrate was achieved in vitro and in vivo. The prototype microcapsules/spheres effectively controlled or eliminated *Staphylococcus aureus* and *Steptococcus Pyogenes* from infected wounds in rats. Additionally, the formulation would be effective in the treatment of all bacterial infections caused by organisms sensitive to the antibiotic encapsulated including but not limited to Enterobacteriaceae; Klebsiella sp.; Bacteroides sp.; Enterococci; Proteus sp.; Streptococcus sp.; Staphylococcus sp.; Pseudomonas sp.; Neisseria sp.; Pedptostreptococcus sp.; Fusobacterium sp.; Actinomyces sp.; Mycobacterium sp.; Listeria sp; Corynebacterium sp.; Pronrionibacterium sp.; Actinobacillus sp; Aerobacter sp.; Borrelia sp.; Campylobacter sp.; Cytophaga sp.; Pasteurella sp.; Clostridium sp.; *Enterobacter aerogenes*; Peptococcus sp.; *Proteus vulgaris; Proteus morganii; Staphylococcus aureus; Streptococcus polygenes*; Actinomyces sp.; *Campylobacter fetus*; and *Legionella pneumophila*. Results indicate that optimal microcapsules/spheres should exhibit a programmed release of an appropriate concentration of antibiotic over about a 14 day to about a 6 week time period after which time the microcapsule/sphere should biodegrade, leaving no trace of drug or excipient.

We claim:

1. A method for the protection against or therapeutic treatment of bacterial infection in the tissue of a human or nonhuman animal comprising administering locally to said animal a bactericidally-effective amount of a pharmaceutical composition consisting essentially of an antibiotic encapsulated within a biodegradable comprising poly (DL-lactide-co-glycolide) matrix wherein the duration of controlled release of the antibiotic is within a period of about 14 days to about 6 weeks.

2. The method according to claim 1 wherein the biodegradable Polymeric matrix is a poly (DL-lactide-co-glycolide having a relative ratio between the amount of lactide and glycolide component within th e range of 40:60 to 100:0.

3. A method according to claim 1 wherein the bacterial infection is (1) a subcutaneous infection secondary to contaminated abdominal surgery, (2) an infection surrounding prosthetic devices and vascular grafts, (3) ocular infections, (4) topical skin infections, (5) orthopedic infections, including osteomyelitis, and (6) oral infections.

4. The method according to claim 3 wherein the oral infections are pericoronitis or periodontal disease.

5. The method according to claim 1 wherein the administration is effected prior to infection.

6. The method according to claim 1 wherein the administration is effected subsequent to infection.

7. The method according to claim 1 wherein said animal is a human.

8. The method according to claim 1 wherein said animal is a nonhuman.

9. The method in accordance with claim 1 comprising applying to the soft tissue or bone tissue of said animal a bactericidally-effective amount of a pharmaceutical composition consisting essentially of an antibiotic in the amount of 5 to 60 percent, selected from the group consisting essentially of a beta-lactam, aminoglycolide, polymyxin-B, Amphotericin B, Aztreonam, cephalosporins, chloramphenicol, fusidans, lincosamides, macrolides, methronidazole, nitro-furation, Imipenem/cilastin, quinolones, refampin, polyenes, tetracycline, sulfonamides, trimethoprim, vancomycin, teicoplanin, imidazoles, and erythromycin, encapsulated within a biodegradable poly(DL-lactide-co-glycolide) polymeric matrix, wherein the amount of the lactide component is within the range of 48 to 58 glycolide component is within the range of 52 to 42 based on the weight of said polymeric matrix which is present in the amount of from 40 to 95 percent, resulting in the controlled release of a bacteriacidal amount of the said antibiotic over a period of about 14 days to about 6 weeks.

10. The method of claim 2 wherein the polymeric matrix consists essentially of a poly(DL-lactide-co-glycolide) wherein the relative ratio between the amount of lactide and glycolide component is within the range of 48:52 to 58:42.

11. The method of claim 9 wherein the bacterial infection is caused by a resistant or non-resistant bacteria selected from the group consisting essentially of Enterobacteriaceae; Klebsiella sp.; Bacteroides sp.; Enterococci; Proteus sp.; Streptococcus sp.; Staphylococcus sp; Pseudomonas sp.; Neisseria sp.; Pedptostreptococcus sp.; Fusobacterium sp.; Actinomyces sp.; Mycobacterium sp.; Listeria sp.; Corynebacterium sp.; Proprionibacterium sp.; Actinobacillus sp.; Aerobacter sp.; Borrelia sp.; Campylobacter sp.; Cytophaga sp.; Pasteurella sp.; Clostridium sp., *Enterobacter aerogenes*, Peptococcus sp., *Proteus vulgaris, Proteus morganii, Staphylococcus aureus, Streptococcus pyogenes*, Actinomyces sp., *Campylobacter fetus*, and *Legionella pneumophila*. Ampicillin-resistant strain of *S. aureus* and methicillin-resistant strain of *S. aureus*.

12. The method of claim 10 wherein the antibiotic is selected from the group consisting essentially of a beta-lactam, aminoglycolide, polymyxin-B, amphotericin B, aztreonam, cephalosporins, chloramphenicol, fusidans, lincosamides, maacrolides, methronidazole, nitro-furantoin, Imipenem/cilastin, quinolones, rifampin, polyenes, tetracycline, sulfonamides, trimethoprim, vancomycin, teicoplanin, imidazoles, and erythromycin.

13. The method of claim 12 wherein the beta-lactam is selected from the group consisting essentially of penicillin and cephalosporin.

14. The method of claim 13 wherein the beta-lactam is cephalosporin.

15. The method of claim 13 wherein the beta-lactam is penicillin.

16. The method of claim 12 wherein the aminoglycolide is gentamicin.

17. The method of claim 12 wherein the aminoglycolide is amikacin.

18. The method of claim 12 wherein the aminoglycolide is tobramycin.

19. The method of claim 12 wherein the aminoglycolide is kanamycin.

20. The method of claim 13 wherein the beta-lactam is an ampicillin.

21. The method of claim 20 wherein the polymeric matrix consists essentially of a poly(DL-lactide-co-glycolide) wherein the relative ratio between the amount of lactide and glycolide component is within the range of 48:52 to 58:42.

22. The method of claim 20 wherein the ampicillin is present in an amount of from 5 to 60 percent and the amount of polymeric matrix is from 40 to 95 percent.

23. The method of claim 22 wherein the amount of ampicillin is 30 to 40 percent and the amount of the poly(DL-Lactide-co-glycolide) is 60 to 70 percent.

24. The method of claim 23 wherein the relative ratio between the amount of lactide and glycolide component is 53:47.

25. The method of claim 13 wherein the beta-lactam is a cefazolin.

26. The method of claim 25 wherein the polymeric matrix consists essentially of a poly(DL-lactide-co-glycolide) wherein the relative ratio between the amount of lactide and glycolide component is within the range of 48:52 to 58:42.

27. The method of claim 25 wherein the cefazolin is present in an amount of from 5 to 60 percent and the amount of polymeric matrix is from 40 to 95 percent.

28. The method of claim 27 wherein the amount of ampicillin is 30 to 40 percent and the amount of the poly(DL-Lactide-co-glycolide) is 60 to 70 percent.

29. The method of claim 28 wherein the relative ratio between the amount of lactide and glycolide component is 53:47.

30. A pharmaceutical composition useful in the effective treatment of an animal with infected wound in the soft-tissue a bone consisting essentially of an antibiotic encapsulated within a biodegradable comprising poly (DL-lactide-co-glycolide) matrix wherein the controlled release rate of the antibiotic is within a period of about 14 days to about 6 weeks.

31. The pharmaceutical composition according to claim 25 comprising an antibiotic in the amount of 5 to 60 percent, selected from the group consisting essentially a beta-lactam, aminoglycolide, polymyxin-B, amphotericin B, azetreonam, cephalosporins, chloramphenicol, fusiduns, lincosamides, macrolides, methronidazole, nitro-fuation, Impenem/cilastin, quinolones, refampin, polyenes, tetracycline, sulfonamides, trimethoprim, vancomycin, teicoplanin, imidazoles, and erythromycin, encapsulated within a biodegradable poly(DL-lactide-co-glycolide) polymeric matrix, wherein the amount of the lacide component is within the range of 48 to 58 glycolide component is within the range of 52 to 42 based on the weight of said polymeric matrix which is present in the amount of from 40 to 95 percent, resulting in the controlled release of a bactericidal amount of said antibiotic over a period of about 14 days to about 6 weeks.

32. The composition of claim 31 wherein the bacteria is selected from the group consisting essentially of Enterobacteriaceae; Klebsiella sp.; Bacteroides sp.; Enterococci; Proteus sp.; Streptococcus sp.; Staphylococcus sp.; Pseudomonas sp.; Neisseria sp.; PedDtostreptococcus sp.; Fusobacterium sp.; Actinomyces sp.; Mycobacterium sp.; Listeria sp.; Corynebacterium sp.; Proprionibacterium sp.; Actinobacillus sp.; Aerobacter sp.; Borrelia sp.; Campylobacter sp.; Cytophaga sp.; Pasteurella sp.; Clostridium sp., *Enterobacter aerogenes*, Peptococcus sp., *Proteus vulgaris, Proteus morganii, Staphylococcus aureus, Streptococcus pryocgenes*, Actinomyces sp., *Camplobacter fetus*, and *Legionella Pneumophila*.

33. The composition of claim 32 wherein the antibiotic is selected from the group consisting essentially of a beta-lactam, aminoglycolide, polymyxin-B, amphotericin B, Aztreonam, cephalosporins, chloramphenicol, fusidans, lincosamides, macrolides, methronidazole, nitro-furantion, imipenem/cilastin, quinolones, rifampin, polyenes, tetracycline, sulfonamides, trimethoprim, vancomycin, teicoplanin, imidazoles, and erythromycin.

34. The composition of claim 33 wherein the beta-lactam is selected from the group consisting essentially of penicillin and cephalosporin.

35. The composition of claim 33 wherein the beta-lactam is cephalosporin.

36. The composition of claim 33 wherein the beta-lactam is penicillin.

37. The composition of claim 33 wherein the aminoglycolide is gentamicin.

38. The composition of claim 33 wherein the aminoglycolide is amikacin.

39. The composition of claim 33 wherein the aminoglycolide is tobramycin.

40. The composition of claim 33 wherein the aminoglycolide is kananycin.

41. The composition of claim 33 wherein the beta-lactam is a ampicillin.

42. The composition of claim 33 wherein the beta-lactam is cefazolin.

43. The composition of claim 41 wherein the polymeric matrix consists essentially of a poly(DL-lactide-co-glycolide) wherein the relative ratio between the amount of the lactide and glycolide component is within the range of 48:52 to 58:42.

44. The composition of claim 43 wherein the amount of ampicillin is from 5 to 60 percent and the amount of polymeric matrix is from 40 to 95 percent.

45. The composition of claim 44 wherein the amount of ampicillin is 30 to 40 percent and the amount of the poly(DL-lactide-co-glycolide) is 60 to 70 percent.

46. The composition of claim 45 wherein the relative ratio between the amount of lactide and glycolide component is 53:47.

47. The composition of claim 45 wherein the ampicillin is ampicillin anhydrate.

* * * * *